(12) United States Patent
Ruiz, Sr. et al.

(10) Patent No.: US 9,066,711 B2
(45) Date of Patent: Jun. 30, 2015

(54) APPLICATORS FOR STORING STERILIZING, AND DISPENSING AN ADHESIVE

(75) Inventors: Rafael Ruiz, Sr., Hudson, NC (US); Sheng Zhang, Hickory, NC (US); Martin Krauss, Fort Myers, FL (US)

(73) Assignee: Adhezion Biomedical, LLC, Wyomissing, PA (US)

( * ) Notice: Subject to any disclaimer, the term of this patent is extended or adjusted under 35 U.S.C. 154(b) by 792 days.

(21) Appl. No.: 13/287,238

(22) Filed: Nov. 2, 2011

(65) Prior Publication Data

US 2013/0108352 A1 May 2, 2013

(51) Int. Cl.
| | | |
|---|---|---|
| *A61M 35/00* | (2006.01) | |
| *A61B 17/00* | (2006.01) | |
| *B65D 35/36* | (2006.01) | |
| *B65D 51/22* | (2006.01) | |
| *A46B 11/00* | (2006.01) | |
| *A61F 13/40* | (2006.01) | |
| *A61B 19/00* | (2006.01) | |

(52) U.S. Cl.
CPC ....... *A61B 17/00491* (2013.01); *A46B 11/0075* (2013.01); *B65D 35/36* (2013.01); *B65D 51/225* (2013.01); *A61M 35/003* (2013.01); *A61M 35/006* (2013.01); *A61B 2019/4868* (2013.01)

(58) Field of Classification Search
USPC .................................. 401/132–135; 604/3
See application file for complete search history.

(56) References Cited

U.S. PATENT DOCUMENTS

| 211,104 | A | 1/1879 | Mulford |
|---|---|---|---|
| 334,046 | A | 1/1886 | Pinkham |
| 1,221,227 | A | 4/1917 | Schulz |
| 1,229,195 | A | 6/1917 | Hamilton |
| 1,234,844 | A | 7/1917 | Williams |
| 1,822,566 | A | 9/1931 | Davies |
| 2,333,070 | A | 10/1943 | Hoey et al. |
| 2,721,858 | A | 10/1955 | Joyner et al. |
| 3,152,352 | A | 10/1964 | Kosik, Jr. |
| 3,254,111 | A | 5/1966 | Hawkins et al. |
| 3,324,855 | A | 6/1967 | Heimlich |
| 3,393,962 | A | 7/1968 | Andrews |
| 3,523,628 | A | 8/1970 | Colvin et al. |
| 3,614,245 | A | 10/1971 | Schwartzman |
| 3,797,706 | A | 3/1974 | Mule |
| 3,924,623 | A | 12/1975 | Avery |
| 3,941,488 | A | 3/1976 | Maxwell |
| 3,945,383 | A | 3/1976 | Bennett et al. |

(Continued)

FOREIGN PATENT DOCUMENTS

| DE | 203 14 688 U1 | 11/2003 |
|---|---|---|
| ER | 1 445 032 | 8/2004 |

(Continued)

OTHER PUBLICATIONS

International Search Report and Written Opinion received in counterpart application PCT/US12/62976 dated Mar. 25, 2013.

*Primary Examiner* — David Walczak
(74) *Attorney, Agent, or Firm* — Stradley Ronon Stevens & Young, LLP

(57) ABSTRACT

Applicators for storing, sterilizing, and dispensing adhesives. The applicators comprise a porous tip, a body, and a container containing a polymerizable cyanoacrylate monomer adhesive. The applicators are sterilized by radiation, and following sterilization, the adhesive remains substantially unpolymerized for about twenty four months.

24 Claims, 12 Drawing Sheets

(56) References Cited

U.S. PATENT DOCUMENTS

| | | | |
|---|---|---|---|
| 4,138,040 | A | 2/1979 | Stock |
| 4,199,915 | A | 4/1980 | Levine |
| 4,271,982 | A | 6/1981 | Niksich et al. |
| 4,408,699 | A | 10/1983 | Stock |
| 4,413,753 | A | 11/1983 | Stock |
| 4,480,940 | A | 11/1984 | Woodruff |
| 4,498,609 | A | 2/1985 | Stock |
| 4,507,111 | A | 3/1985 | Gordon et al. |
| 4,685,591 | A | 8/1987 | Schaefer et al. |
| 4,687,827 | A | 8/1987 | Russo |
| 4,724,177 | A | 2/1988 | Russo |
| 4,772,148 | A | 9/1988 | Buschemeyer |
| 4,777,085 | A | 10/1988 | Murray, Jr. et al. |
| 4,784,506 | A | 11/1988 | Koreska et al. |
| 4,844,250 | A | 7/1989 | Holubek et al. |
| 4,979,638 | A | 12/1990 | Bolduc |
| 5,006,004 | A | 4/1991 | Dirksing et al. |
| 5,013,172 | A | 5/1991 | Menrath |
| 5,016,784 | A | 5/1991 | Batson |
| 5,018,643 | A | 5/1991 | Bolduc |
| 5,031,384 | A | 7/1991 | Rebeyrolle et al. |
| 5,042,690 | A | 8/1991 | O'Meara |
| 5,052,585 | A | 10/1991 | Bolduc |
| 5,131,777 | A | 7/1992 | Kimura et al. |
| 5,133,458 | A | 7/1992 | Miller |
| 5,154,320 | A | 10/1992 | Bolduc |
| 5,171,149 | A | 12/1992 | Alpert |
| 5,226,562 | A | 7/1993 | Kirk |
| 5,232,774 | A | 8/1993 | Otsuka et al. |
| 5,263,615 | A | 11/1993 | Anderson et al. |
| 5,288,159 | A | 2/1994 | Wirt |
| 5,324,131 | A | 6/1994 | Gardner, III |
| 5,344,670 | A | 9/1994 | Palmer et al. |
| 5,358,349 | A | 10/1994 | Burroughs et al. |
| 5,379,927 | A | 1/1995 | Montenieri et al. |
| 5,411,345 | A | 5/1995 | Ueji et al. |
| 5,649,648 | A | 7/1997 | Lier et al. |
| 5,658,384 | A | 8/1997 | Imlay, Jr. |
| 5,665,106 | A | 9/1997 | Hammerslag |
| 5,665,107 | A | 9/1997 | Hammerslag |
| 5,749,665 | A | 5/1998 | Kato et al. |
| 5,759,194 | A | 6/1998 | Hammerslag |
| 5,769,552 | A | 6/1998 | Kelley et al. |
| 5,810,495 | A | 9/1998 | McAuley |
| D402,199 | S | 12/1998 | Saunders |
| 5,888,007 | A | 3/1999 | Nicoll et al. |
| 5,906,300 | A | 5/1999 | Horie |
| 5,909,976 | A | 6/1999 | Maeda |
| 5,928,611 | A | 7/1999 | Leung |
| 5,971,225 | A | 10/1999 | Kapsa |
| 5,996,796 | A | 12/1999 | Kvitrud et al. |
| 6,099,807 | A | 8/2000 | Leung |
| 6,155,265 | A | 12/2000 | Hammerslag |
| 6,217,603 | B1 | 4/2001 | Clark et al. |
| 6,283,933 | B1 | 9/2001 | D'Alessio et al. |
| 6,322,852 | B1 | 11/2001 | Leung |
| 6,331,172 | B1 | 12/2001 | Epstein et al. |
| 6,340,097 | B1 | 1/2002 | D'Alessio et al. |
| 6,372,313 | B1 | 4/2002 | D'Alessio et al. |
| 6,376,019 | B1 | 4/2002 | Leung |
| 6,425,704 | B2 | 7/2002 | Voiers et al. |
| 6,428,233 | B1 | 8/2002 | Clark et al. |
| 6,428,234 | B1 | 8/2002 | Bobo et al. |
| 6,439,789 | B1 | 8/2002 | Ballance et al. |
| 6,475,502 | B1 | 11/2002 | Lee et al. |
| 6,478,191 | B1 | 11/2002 | D'Alessio et al. |
| 6,488,665 | B1 | 12/2002 | Severin et al. |
| 6,492,434 | B1 | 12/2002 | Barley, Jr. et al. |
| 6,494,896 | B1 | 12/2002 | D'Alessio et al. |
| 6,505,985 | B1 | 1/2003 | Hidle et al. |
| 6,506,464 | B1 | 1/2003 | Montenieri et al. |
| 6,541,304 | B1 | 4/2003 | Bouras et al. |
| 6,547,467 | B2 | 4/2003 | Quintero |
| 6,550,644 | B2 | 4/2003 | Cruddas |
| 6,557,731 | B1 | 5/2003 | Lyon et al. |
| 6,592,281 | B2 | 7/2003 | Clark et al. |
| 6,595,940 | B1 | 7/2003 | D'Alessio et al. |
| 6,616,019 | B2 | 9/2003 | D'Alessio et al. |
| 6,637,967 | B2 | 10/2003 | Bobo et al. |
| 6,672,456 | B2 | 1/2004 | Russell |
| 6,676,322 | B1 | 1/2004 | Leung |
| 6,676,332 | B1 | 1/2004 | Hauer et al. |
| 6,705,467 | B1 | 3/2004 | Kancsar et al. |
| 6,705,790 | B2 | 3/2004 | Quintero et al. |
| 6,779,657 | B2 | 8/2004 | Mainwaring et al. |
| 6,802,416 | B1 | 10/2004 | D'Alessio et al. |
| 6,811,341 | B2 | 11/2004 | Crane |
| 6,817,802 | B2 | 11/2004 | Nishitani et al. |
| 6,863,460 | B2 | 3/2005 | Nicoll et al. |
| 6,960,040 | B2 | 11/2005 | D'Alessio et al. |
| 6,981,664 | B1 | 1/2006 | Fugere |
| 7,040,827 | B2 | 5/2006 | Gueret |
| 7,094,250 | B2 | 8/2006 | Stenton |
| 7,128,241 | B2 | 10/2006 | Leung |
| 7,179,008 | B2 | 2/2007 | Holcomb |
| 7,297,217 | B2 | 11/2007 | Dewitt |
| 7,306,390 | B2 | 12/2007 | Quintero et al. |
| RE40,003 | E | 1/2008 | Bennett et al. |
| 7,316,833 | B1 | 1/2008 | Galloway et al. |
| 7,434,692 | B2 | 10/2008 | Ginsberg et al. |
| 7,441,973 | B2 | 10/2008 | Voegele et al. |
| 7,516,872 | B2 | 4/2009 | Boone et al. |
| 7,621,411 | B2 | 11/2009 | Doherty et al. |
| 7,648,296 | B2 | 1/2010 | Wong |
| 7,696,399 | B2 | 4/2010 | Rogers |
| 7,704,003 | B2 | 4/2010 | Ziniti et al. |
| 7,708,180 | B2 | 5/2010 | Murray et al. |
| 7,744,624 | B2 | 6/2010 | Bettuchi |
| 7,785,026 | B2 | 8/2010 | Eng et al. |
| 7,918,621 | B2 * | 4/2011 | Battisti ........................ 401/134 |
| 8,100,294 | B2 * | 1/2012 | May et al. ..................... 222/129 |
| 8,118,508 | B2 | 2/2012 | Goodman et al. |
| 2002/0151873 | A1 | 10/2002 | Moore |
| 2005/0025559 | A1 | 2/2005 | Stenton |
| 2005/0047845 | A1 | 3/2005 | White et al. |
| 2005/0047846 | A1 | 3/2005 | Narang et al. |
| 2005/0054967 | A1 | 3/2005 | Ashe et al. |
| 2005/0147457 | A1 | 7/2005 | Badejo et al. |
| 2005/0147582 | A1 | 7/2005 | Zimmerman et al. |
| 2005/0148998 | A1 | 7/2005 | Haley |
| 2005/0175395 | A1 | 8/2005 | Quintero et al. |
| 2005/0196431 | A1 | 9/2005 | Narang et al. |
| 2005/0256446 | A1 | 11/2005 | Criscuolo et al. |
| 2006/0049203 | A1 | 3/2006 | Boone et al. |
| 2006/0247568 | A1 | 11/2006 | Stenton |
| 2006/0282035 | A1 | 12/2006 | Battisti et al. |
| 2007/0078207 | A1 | 4/2007 | Jonn et al. |
| 2007/0084144 | A1 | 4/2007 | Labrecque et al. |
| 2007/0131356 | A1 | 6/2007 | Battisti |
| 2007/0147947 | A1 | 6/2007 | Stenton et al. |
| 2008/0033280 | A1 | 2/2008 | Lubock et al. |
| 2008/0058863 | A1 | 3/2008 | Quintero et al. |
| 2008/0069801 | A1 | 3/2008 | Lee et al. |
| 2008/0095569 | A1 | 4/2008 | Voegele et al. |
| 2008/0105580 | A1 | 5/2008 | Netwick et al. |
| 2008/0121657 | A1 | 5/2008 | Voegele et al. |
| 2008/0125811 | A1 | 5/2008 | Bettuchi |
| 2008/0131190 | A1 | 6/2008 | Goodman et al. |
| 2008/0167681 | A1 | 7/2008 | Stenton |
| 2008/0195040 | A1 | 8/2008 | Clark et al. |
| 2008/0241249 | A1 | 10/2008 | Quintero et al. |
| 2008/0245314 | A1 | 10/2008 | Brodowski et al. |
| 2008/0287987 | A1 | 11/2008 | Boyden et al. |
| 2008/0319063 | A1 | 12/2008 | Zhang |
| 2009/0257976 | A1 | 10/2009 | Kerber et al. |
| 2009/0311030 | A1 | 12/2009 | Stenton |
| 2009/0317353 | A1 | 12/2009 | Zhang et al. |

(56) References Cited

U.S. PATENT DOCUMENTS

| | | |
|---|---|---|
| 2009/0318583 A1 | 12/2009 | Zhang et al. |
| 2009/0324319 A1 | 12/2009 | Houde et al. |
| 2009/0324320 A1 | 12/2009 | Houde et al. |
| 2010/0168637 A1 | 7/2010 | Casey et al. |
| 2010/0168638 A1 | 7/2010 | Korogi et al. |
| 2010/0274258 A1 | 10/2010 | Silvestrini et al. |
| 2011/0028883 A1 | 2/2011 | Juan, Jr. et al. |
| 2012/0070220 A1 | 3/2012 | Ruiz, Sr. et al. |

FOREIGN PATENT DOCUMENTS

| | | |
|---|---|---|
| FR | 1130737 | 10/1956 |
| FR | 2700698 | 7/1994 |
| GB | 1016053 | 1/1966 |
| JP | 58-41068 | 3/1983 |
| JP | 2006-315307 | 11/2006 |

* cited by examiner

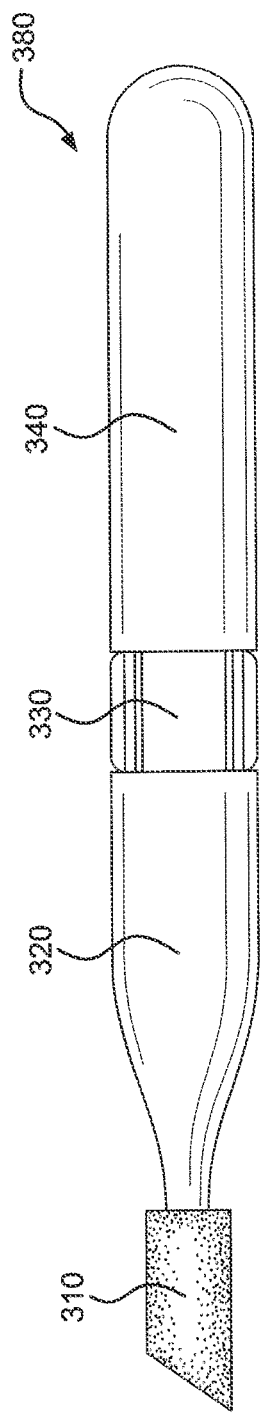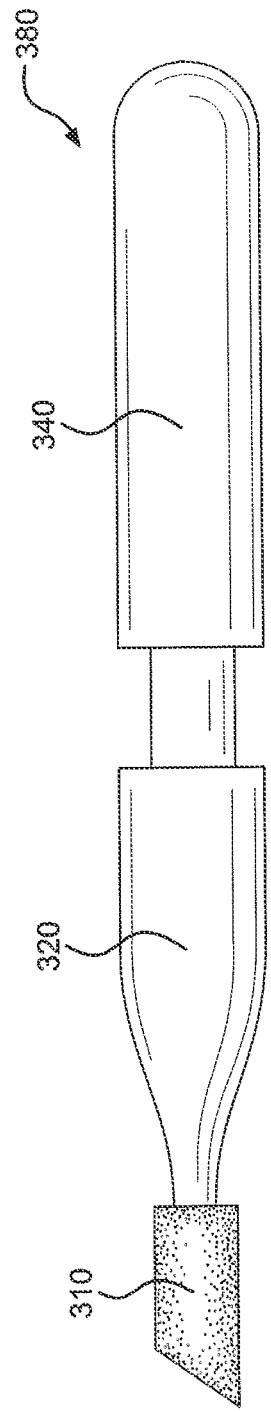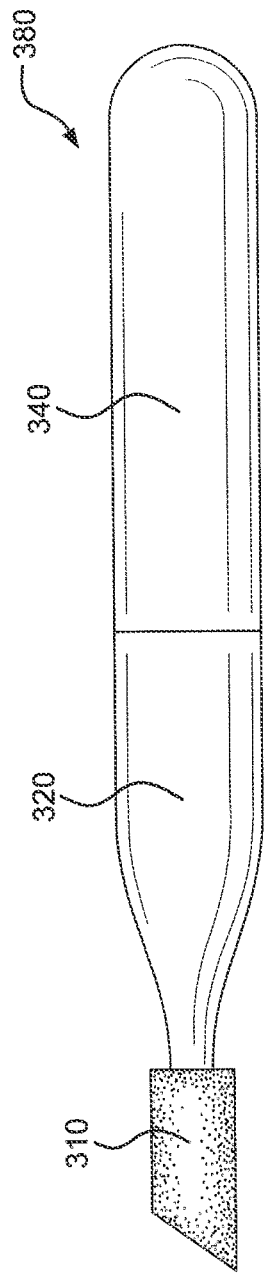

APPLICATORS FOR STORING STERILIZING, AND DISPENSING AN ADHESIVE

FIELD OF INVENTION

This invention relates generally to the field of adhesive applicator devices. More particularly, the invention relates to sterilizable applicators for storing and applying adhesives.

BACKGROUND

Various publications, including patents, published applications, technical articles and scholarly articles are cited throughout the specification. Each of these cited publications is incorporated by reference herein, in its entirety and for all purposes.

A large number of dispensing and packaging systems for cyanoacrylate-based adhesive and/or sealant material have been proposed. U.S. Pat. No. 4,413,753 to Stock discloses a self-draining tip for dispensing cyanoacrylate adhesives. The dispensing tip includes a single or segmented constant diameter passageway having sharp-edged annular terminations for dispensing. U.S. Pat. No. 4,685,591 to Schaefer et al. discloses a packaging tube that is suitable for storing and dispensing products containing substantial fractions of cyanoacrylates. The tube sidewall is made of multi-layer sheet material and a covering strip is placed over the inside surface the tube.

U.S. Pat. No. 5,649,648 to Lier et al. discloses a packaging system for free-flowing material such as cyanoacrylate adhesive. The package comprises a container and a closable applicator point fitted on its outlet aperture. The container is made of an extruded receptacle aluminum that springs back when the pressure is released.

U.S. Pat. No. 6,547,467 to Quintero discloses a microapplicator for dispensing and applying cyanoacrylate-based adhesive. The microapplicator comprises a handle portion, a microreservoir at the applicator tip to hold about 20 microliter or less, of adhesive material. The applicator tip may include a spatula, a rolling ball, a grate, a porous material, and a brush. U.S. Pat. No. 6,779,657 to Mainwaring et al. discloses a single-use applicator assembly for applying and dispensing cyanoacrylate monomeric adhesive material. The applicator comprises a base with at least one sealed container and an applicator tip at least partially disposed in the container such that the tip of the applicator has access to the adhesive material. U.S. Pat. No. 7,297,217 to Dewitt discloses a dispenser for application of a special low viscosity cyanoacrylate adhesive which is used for the manufacture and repair of wooden furniture. The dispenser is provided with a closure member having a metallic pin that penetrates the discharge opening while the closure member is being secured thereon.

U.S. Publ. No. 2006/0282035 to Battisti et al. discloses a disposable swab applicator for containing and dispensing cyanoacrylate adhesive. The swab applicator is closed at one end and covered by a swab applicator with the cyanoacrylate composition contained by a valve that can be easily opened when desired. The valve can be a ball, a bead or a capsule. The device can be heat sterilized using dry heat sterilization.

U.S. Publ. No. 2007/0147947 to Stenton et al. discloses an applicator for forming uniform thickness layers of liquid coating on a substrate surface. The applicator is characterized by controlling the dispensing of liquid through apertures incorporated within the applicator head. The applicator uses a supported thin layer of foam which assures uniform thickness of applied layers, which are substantially independent of the pressure applied to the applicator.

U.S. Publ. No. 2008/0105580 to Nentwick et al. discloses an applicator tip for dispensing a cyanoacrylate-based adhesive from a reservoir. The applicator tip includes an opening offset and a distal end. The adhesive material is dispensed when pressure is applied to the applicator tip surface so that the applicator tip is in a deformed configuration.

U. S. Publ. No. 2008/0167681 to Stenton discloses an adhesive applicator for applying medical adhesives to surgical incisions. The applicator comprises a receiver having a deformable cylindrical body, a blunt cylindrical body with an adhesive-permeable foam material, a frangible ampule containing adhesive material, and a pair of wings having a pressure barb facing toward the cylindrical wall to break the frangible ampule.

Cyanoacrylate-based adhesive, Dermabond® (Johnson & Johnson, New Brunswick, N.J.) was approved by US FDA in 1998 to be used as topical wound closure adhesive. In order to apply and dispense Dermabond® (Johnson & Johnson, New Brunswick, N.J.) and related adhesive products, a series of patents or patent applications with regard to the applicator and/or dispenser have been developed. For example, U.S. Publ. No. 2005/0175395, U.S. Pat. Nos. 7,306,390 and 6,705, 790 to Quintero et al. discloses an applicator assembly for dispensing adhesive material. The applicator comprises first and second body portions, a frangible ampule container for adhesive, and a breaking member to rupture the container for dispensing the adhesive material.

U.S. Pat. Nos. 6,960,040, 6,494,896, and 6,340,097 to D'Alessio et al. disclose package assembly suitable for laparoscopic or endoscopic surgery. U.S. Pat. Nos. 7,128,241, 6,676,322, 6,376,019, 6,322,852, 6,099,807, 5,928,611 to Leung discloses an applicator tip for dispensing cyanoacrylate adhesive stored in a frangible glass ampule container. The porous, absorbent applicator tip includes a polymerization initiator to accelerate the polymerization of cyanoacrylate adhesive when applied.

The Dermabond® (Johnson & Johnson, New Brunswick, N.J.) applicator associated with most patents mentioned above comprises a glass ampule for storing adhesives and a porous applicator tip incorporating a polymerization initiator. As published by FDA in the Maude Adverse Event Report, the glass vial of the Dermabond® (Johnson & Johnson, New Brunswick, N.J.) applicator was crushed and the shard protruded through the tube, penetrated the gloves and pierced the hands of the medical professionals or the patients. The shard penetration adverse effect of Dermabond® (Johnson & Johnson, New Brunswick, N.J.) occurred repeatedly since it was marketed. The breakage or rupture of broken glass through the outside plastic package exposes the user or patient to risk. Another problem associated with this type of applicator is the clogging of the applicator tip. The presence of polymerization initiator in the applicator tip can lead to rapid polymerization of cyanoacrylate adhesives to clog the applicator, which causes the waste of adhesive material. The clogging of the applicator may delay the wound closure process during surgery, which may result in problems for both patients and surgical professionals.

The prior applicator devices may possess other shortcomings besides the clogging and safety problem. The lack of flow rate control of adhesive is one of the issues surgical doctors often face. A further inconvenience which has occurred in prior applicators is the requirement of two hands to operate. Furthermore, the design and dispensing mechanism of some of the prior applicators are very complicated and thereby very expensive. More importantly, the known applicators fail to be compatible with radiation sterilization techniques so that cyanoacrylate adhesives inside either cannot be sterilized by radiation, such as electron beam, gamma, and x-ray, or cannot provide a stable shelf life after sterilization in such applicator. Therefore, a need exists for new applicator designs, which are easy to use, safe due to the absence of glass, capable of controlling flow rate, compatible with radiation sterilization techniques, exhibits no clogging of the applicator tip, and causes no waste of adhesives.

SUMMARY

This invention provides applicators which address the need for an easy to use, safe and efficient package system for applying and dispensing an adhesive material. Various applicators disclosed herein are designed to store, sterilize, and dispense adhesive compositions. The adhesive compositions are preferably polymerizable 1,1-disbustituted ethylene monomers, and more preferably the adhesive compositions are based on cyanoacrylate monomers.

In some aspects, an applicator for storing and dispensing an adhesive comprises a container comprising walls defining a chamber having an opening at the distal end and fabricated from a material that is substantially impermeable to moisture and air, a distal seal, a middle seal, and a proximal seal, and a polymerizable cyanoacrylate monomer adhesive stored in the chamber between the proximal seal and the proximal end of the container, a body comprising a flange comprising at least one hole, a channel in communication with the hole, extending distally through the body, and having an opening at the distal end, and optionally, a grip capable of constricting the channel when inward pressure is applied to the grip, with the proximal end of the flange positioned between the middle seal and the proximal seal of the container and being capable of penetrating the proximal seal when the body and the container are compressed together; a porous tip in communication with the opening at the distal end of the channel; and optionally, a removable lock between the container and the body that prevents the body and the container from being compressed together and that when removed allows the body and the container to be compressed together. The applicator may be activated, for example, releasing the adhesive from the container, by compressing the body and the container together, and the compressing together of the body and container causes the flange to penetrate the proximal seal, which in turn and allows the adhesive to flow into the hole, into and through the channel, and into and out of the porous tip.

The adhesive may be bioabsorbable or non-bioabsorbable. Non-limiting examples of suitable adhesives include 2-octyl cyanoacrylate, dodecyl cyanoacrylate, 2-ethylhexyl cyanoacrylate, butyl cyanoacrylate, methyl cyanoacrylate, 3-methoxybutyl cyanoacrylate, 2-butoxyethyl cyanoacrylate, 2-isopropoxyethyl cyanoacrylate, 1-methoxy-2-propyl cyanoacrylate, or a combination thereof. 2-octyl cyanoacrylate and n-butyl cyanoacrylate are non-limiting examples of non-bioabsorbable adhesives.

The walls of the container portion of the applicator may comprise an acrylonitrile copolymer. The walls of the container may comprise a single layer of an acrylonitrile copolymer, or may comprise a plurality of layers, whereby the acrylonitrile copolymer comprises the inner-most layer of the wall such that the acrylonitrile copolymer layer contacts the adhesive stored in the container. In some aspects, the walls or layers thereof of the container may comprise an acrylonitrile copolymer and methyl acrylate.

The applicator may be sterilized by ionizing radiation. In some aspects, the applicator and the adhesive stored within its container is sterilized by gamma, electron beam, or x-ray radiation, and after the radiation exposure, the adhesive is capable of remaining substantially unpolymerized when stored within the container for a period of at least about six months, at least about twelve months, or at least about twenty four months following sterilization, when stored at room temperature and normal indoor humidity levels.

The porous tip may comprises a swab, sponge, foam, or a brush. Optionally, a tip overlay may be included with the tip.

In some aspects, an applicator for storing and dispensing an adhesive comprises a flexible handle comprising a housing for containing a removable adhesive container and a female end of a luer lock at the distal end of the handle, a body comprising a male end of a luer lock at the proximal end of the body and capable of connecting with the female end at the distal end of the handle, and a channel extending distally through the body, and having an opening at the distal end, a porous tip in communication with the opening at the distal end of the channel, and a removable adhesive container fabricated from a material that is substantially impermeable to moisture and air and capable of fitting within the housing, comprising a frangible seal at the distal end of the container, and a polymerizable cyanoacrylate monomer adhesive stored in the container. The applicator may be activated, for example, by releasing the adhesive from the container, for example, by compromising (e.g., breaking, tearing, puncturing) the frangible seal, and compromising the seal in turn allows the adhesive to flow into and through the channel, and into and out of the porous tip.

The adhesive may be bioabsorbable or non-bioabsorbable. Non-limiting examples of suitable adhesives include 2-octyl cyanoacrylate, dodecyl cyanoacrylate, 2-ethylhexyl cyanoacrylate, butyl cyanoacrylate, methyl cyanoacrylate, 3-methoxybutyl cyanoacrylate, 2-butoxyethyl cyanoacrylate, 2-isopropoxyethyl cyanoacrylate, 1-methoxy-2-propyl cyanoacrylate, or a combination thereof. 2-octyl cyanoacrylate and n-butyl cyanoacrylate are non-limiting examples of non-bioabsorbable adhesives.

The container, which is preferably removable, may comprise an acrylonitrile copolymer. The container may comprise a single layer of an acrylonitrile copolymer, or may comprise a plurality of layers, whereby the acrylonitrile copolymer comprises the inner-most layer of the container such that the acrylonitrile copolymer layer contacts the adhesive stored in the container. In some aspects, the container may comprise an acrylonitrile copolymer and methyl acrylate. The container may be a stick pack container. The frangible seal may comprise a foil, for example, aluminum foil, and may be laminated with an acrylonitrile copolymer.

The applicator may be sterilized by ionizing radiation. In some aspects, the applicator and the adhesive stored within its container is sterilized by gamma, electron beam, or x-ray radiation, and after the radiation exposure, the adhesive is capable of remaining substantially unpolymerized when stored within the container for a period of at least about six months, at least about twelve months, or at least about twenty four months following sterilization, when stored at room temperature and normal indoor humidity levels.

The porous tip may comprises a swab, sponge, foam, or a brush. Optionally, a tip overlay may be included with the tip.

In some aspects, an applicator for storing and dispensing an adhesive comprises a container comprising walls defining a chamber having an opening at the distal end and fabricated from a material that is substantially impermeable to moisture and air, a frangible seal covering the opening, a polymerizable cyanoacrylate monomer adhesive stored in the chamber, and optionally, screw threads on the exterior of the walls, a body comprising a cavity at the proximal end, a channel in communication with the cavity, extending distally through the body, and having an opening at the distal end, a grip capable of constricting the channel when inward pressure is applied to the grip, at least one projection in the cavity, with the projection being capable of penetrating the frangible seal when the body and the container are compressed together, and optionally, screw threads on the walls of the cavity, a porous tip in communication with the opening at the distal end of the channel; and optionally, a removable lock between the container and the body that prevents the body and the container from being compressed together and that when removed allows the body and the container to be compressed together. The applicator may be activated, for example, by compressing the body and the container together, including by rotating the body and container about an axis designated by the screw threads (which may be, for example, in a clockwise or counterclockwise direction) thereby compromising (e.g., breaking, tearing, puncturing) the frangible seal, and compromising the seal in turn allows the adhesive to flow into and through the channel, and into and out of the porous tip.

The adhesive may be bioabsorbable or non-bioabsorbable. Non-limiting examples of suitable adhesives include 2-octyl cyanoacrylate, dodecyl cyanoacrylate, 2-ethylhexyl cyanoacrylate, butyl cyanoacrylate, methyl cyanoacrylate, 3-methoxybutyl cyanoacrylate, 2-butoxyethyl cyanoacrylate, 2-isopropoxyethyl cyanoacrylate, 1-methoxy-2-propyl cyanoacrylate, or a combination thereof. 2-octyl cyanoacrylate and n-butyl cyanoacrylate are non-limiting examples of non-bioabsorbable adhesives.

The walls of the container portion of the applicator may comprise an acrylonitrile copolymer. The walls of the container may comprise a single layer of an acrylonitrile copolymer, or may comprise a plurality of layers, whereby the acrylonitrile copolymer comprises the inner-most layer of the wall such that the acrylonitrile copolymer layer contacts the adhesive stored in the container. In some aspects, the walls or layers thereof of the container may comprise an acrylonitrile copolymer and methyl acrylate. The frangible seal may comprise a foil, for example, aluminum foil, and may be laminated with an acrylonitrile copolymer.

The applicator may be sterilized by ionizing radiation. In some aspects, the applicator and the adhesive stored within its container is sterilized by gamma, electron beam, or x-ray radiation, and after the radiation exposure, the adhesive is capable of remaining substantially unpolymerized when stored within the container for a period of at least about six months, at least about twelve months, or at least about twenty four months following sterilization, when stored at room temperature and normal indoor humidity levels.

The porous tip may comprises a swab, sponge, foam, or a brush. Optionally, a tip overlay may be included with the tip.

BRIEF DESCRIPTION OF THE DRAWINGS

The invention is best understood from the following detailed description when read in connection with the accompanying drawings. It is emphasized that, according to common practice, the various features of the drawings are not to scale. On the contrary, the dimensions of the various features are arbitrarily expanded or reduced for clarity. Included in the drawings are the following figures:

FIG. 7A is a perspective view of a third exemplary applicator of this invention with a lock in place.

FIG. 7B is a perspective view of the applicator shown in FIG. 7A, with the lock removed.

FIG. 7C is a perspective view of the applicator shown in FIGS. 7A and 7B with the body and container compressed together.

DETAILED DESCRIPTION OF THE PREFERRED EMBODIMENTS

This invention relates to dispensers and/or applicators for storing, sterilizing and applying an adhesive or sealant material such as a polymerizable cyanoacrylate monomer. The applicators are designed to be safe and easy to use, with the ability to control the flow rate of an adhesive or sealant material, and compatible with radiation sterilization techniques. In particular, the containers for the adhesive and sealant material of the applicators are made of materials with high moisture and air barrier properties such as acrylonitrile copolymers so that the adhesive and sealant material can be sterilized by radiation and thereafter provide long-term shelf stability.

In some aspects of the invention, an adhesive applicator comprises the following basic components: a body, a container for containing an adhesive material, and a tip. Adhesives may be pre-packaged in the applicator in the container portion, for example, sealed within the container by a frangible foil or a membrane, which may be hermetically sealed. The container for adhesives can be fabricated from a multi-layer sheet material, and the inner layer of the container, which contacts the adhesive, can be fabricated from an acrylonitrile copolymer. The container thereby constructed is compatible with radiation sterilization, such as electron beam, gamma or x-ray sterilization, so that adhesives inside the applicator can be sterilized via radiation without diminished shelf stability (e.g., without prematurely polymerizing). The long-term shelf life stability of adhesive packaged in said applicators may be provided after radiation sterilization.

Figure 1A:
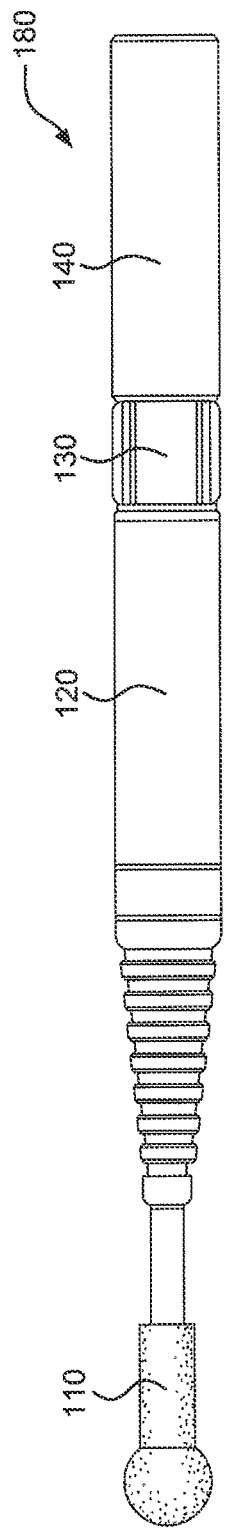
FIG. 1A is a perspective view of a first exemplary applicator of this invention with a lock in place.
Figure 1B:
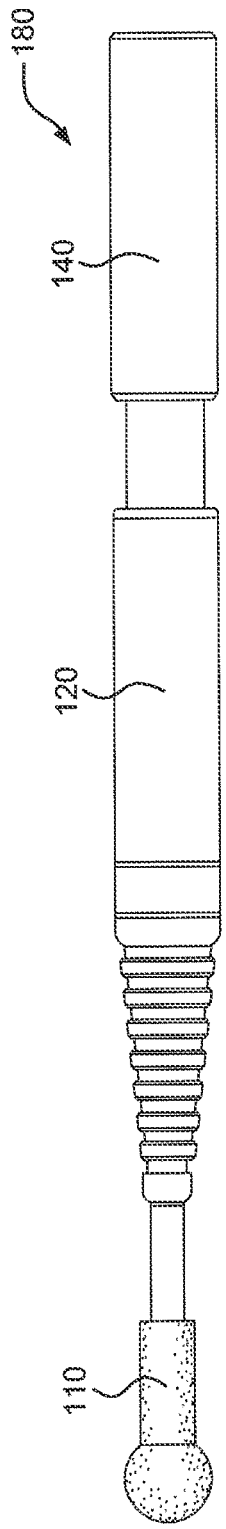
FIG. 1B is a perspective view of the applicator shown in FIG. 1A, with the lock removed.
Figure 1C:
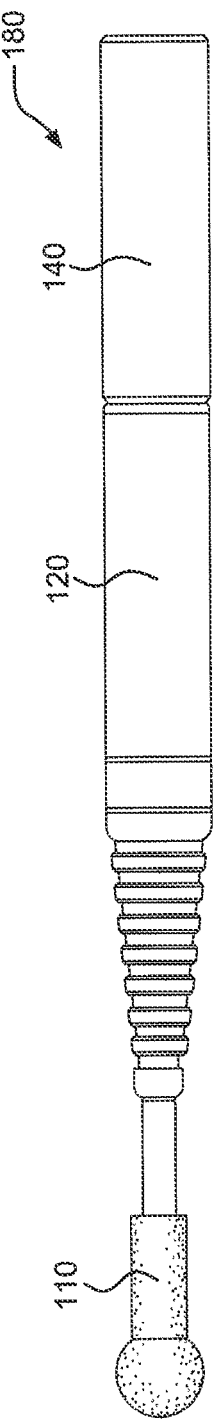
FIG. 1C is a perspective view of the applicator shown in FIGS. 1A and 1B with the body and container compressed together.
Figure 2:
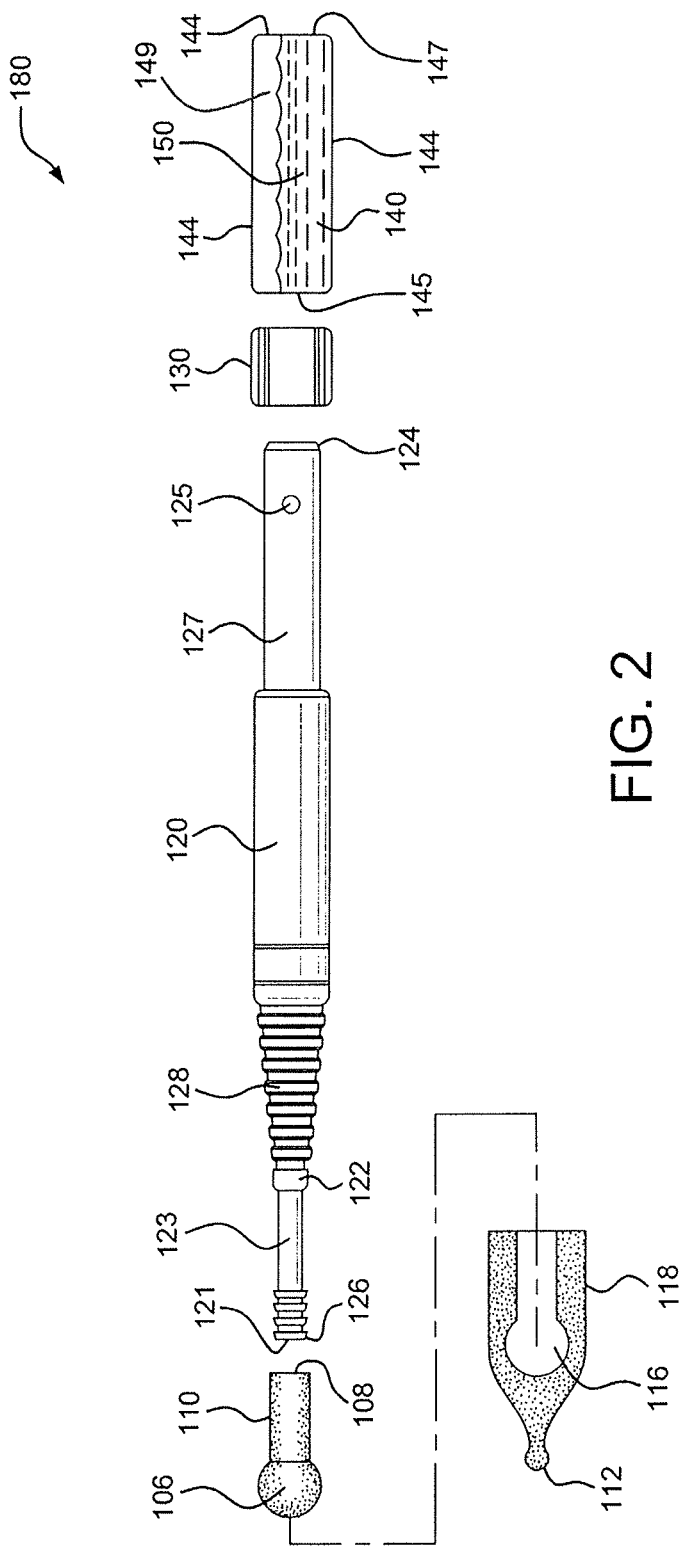
FIG. 2 is an exploded view of the exemplary embodiment of FIG. 1A-C.
Figure 3:
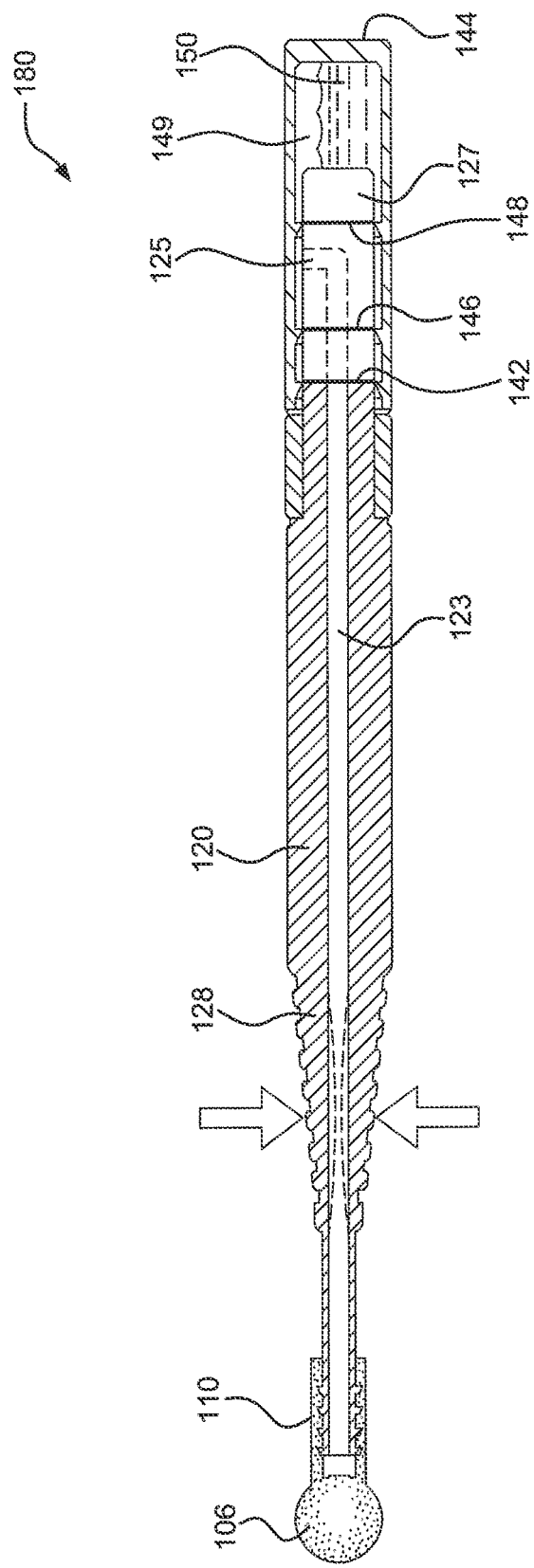
FIG. 3 is a cross-sectional view of the exemplary embodiment of FIG. 1A-C.

FIGS. 1-3 illustrate one non-limiting embodiment of the invention. As shown in FIGS. 1 and 2, an applicator 180 is composed of an applicator tip 110, an applicator body 120, an optional lock 130, and a container 140. The lock 130 is designed to prevent the applicator 180 from accidental activation by keeping the body 120 and container 140 separated until the user removes the lock 130 and brings them together. Once the lock 130 is removed, the applicator body 120 and the container 140 are movable relative to each other, for example, by being compressed together.

FIGS. 2 and 3 show an exploded view and a cross-sectional view of the first embodiment of the present invention, respectively. The applicator body 120 has a distal end 126, and this distal end 126 can fit inside of the proximal end 108 of the applicator tip 110. The connection between the applicator tip 110 and the applicator body 120 may be, for example, a snap-lock fit, a luer lock fit, a screw-cap fit, or a friction fit, and is capable of substantially reducing, inhibiting, or preventing leaking of an adhesive 150 out from the junction of the tip 110 and body 120. The applicator body 120 may include a flow restrictor 122, a grip 128, a flange 127 which has at least one hole 125, and a channel 123 having an opening 121 at its distal end, as shown in FIGS. 2 and 3. The hole 125 and the channel 123 are in communication and serve to have access to, and as a conduit for an adhesive 150 stored in the container 140.

The container 140 comprises a plurality of walls 144 that define a chamber 149 that is preferably open at the distal end 145, which may be closed off by a plurality of seals, for example, a distal seal 142, a middle seal 146, and a proximal seal 148 such as those shown in the cross-sectional view in FIG. 3. A wall 144 is present at the proximal end 147 of the container 140.

A removable lock 130 may be included between the applicator body 120 and the container 140. When the lock 130 is in place in the applicator 180 or otherwise before the applicator 180 is activated, the proximal end of the flange 127, where the hole 125 is preferably located, is in a position between the middle seal 146 and the proximal seal 148 so that the hole 125 has no access to the adhesive 150 being stored in the container 140. When the lock 130 is removed or is otherwise not present, the distal end 145 of the container 140 and the proximal end 124 of the applicator body 120 can be moved toward each other. When the container 140 and the body 120 are compressed together, the flange 127, including the proximal end 124 of the body 120 punctures and passes through the proximal seal 148, and moves inside the container 140 thereby allowing the hole 125 to access the adhesive 150, allowing the adhesive 150 to flow into the hole 125, and through the channel 123.

In order to activate the applicator 180, the lock 130, if present, is removed. Thereafter, the applicator container 140 may be moved by a user toward the applicator body 120. For example, a user may push downward on the proximal end 147 wall 144 of the container 140, for example, with a finger or thumb, while the applicator 180 is held in the user's hand. Once the container 140 and body 120 are pushed together, the hole 125 is pushed beyond the proximal seal 148 and moved into the container 140 so that the adhesive 150 can flow through the hole 125, into the channel 123, through the opening 121 at the distal end 126 of the applicator body 120, and into a porous applicator tip 106. As the adhesive 150 exits the porous applicator tip 106, the user may apply the adhesive 150 to a desired surface.

The release/dispense mechanism is not limited to the specific embodiment shown in FIGS. 1-3. The hole 125 and the channel 123 can be in different positions. The relative positioning of the hole 125 to the seals 142, 146, 148 can be designed using other suitable mechanisms.

The distal seal 142, middle seal 146, and proximal seal 148 may be hermetical seals, and may be made of any suitable material, including a rubber material, a plastic material, a polymer material, a foil material, a composite material, and other known materials that allow the flange 127 and proximal end 124 of the body 120 to penetrate the seals 142, 146, and 148 and pass into the container 140 readily while maintaining a sufficient seal between the body 120 and the container 140 to substantially reduce, inhibit, or prevent leakage of the adhesive 150 at the junction of the body 120 and the container 140 during use. Preferably, the proximal seal 148 is laminated or otherwise coated with an acrylonitrile copolymer, such as those described in this specification.

The grip 128 of the applicator body 120 allows a user to conveniently hold and position the applicator 180 during use. For example, a user may hold the grip 128 similar to how a pen is held, between the thumb and one or more fingers. The grip 128 may itself be comprised of a flexible material that allows the user to squeeze the grip 128 inward, or may comprise a flow restrictor 122 that the user may be able to squeeze, move, or adjust inward toward the channel. Constricting the grip 128 or the flow restrictor 122 may in turn constrict the channel 123, which itself is preferably comprised of a flexible material, in order to control the flow of the adhesive 150 through the channel 123. The flow rate of adhesive 150 may be controlled, for example, by the user providing a desired amount of pressure on the grip 128 or flow restrictor 122 of the applicator body 120. A desired amount of adhesive 150 can thus be dispensed by applying a desired amount of force to the flow restrictor 122 or grip 128.

The applicator tip 110 may be connected to the distal end 126 of the applicator body 120 with any suitable connection, such as a friction fit, a luer lock, a screw cap, or snap-fit. The applicator tip 110 preferably fits tightly into the distal end 126 of the applicator body 120 to substantially reduce, inhibit, or prevent any leakage of adhesive 150 flowing through the applicator 180 from this junction. The applicator tip 110 allows the adhesive 150 to be applied to a desired surface, for example, skin, in a controlled manner.

The tip 110, including the porous applicator tip 106, may be comprised of a porous material, including a fibrous swab, a sponge, foam, bristles, and other suitable materials that allow an adhesive 150 to flow through and out of the porous applicator tip 106. The applicator tip 110, including the porous applicator tip 106 may be fabricated from any suitable materials, including but not limited to foams, rubber, plastics, thermosets, films, cotton, alginate, or membranes. The foam material may be, but is not limited to, polyolefin foam, polyether polyurethane foam, polyester polyurethane foam, high density polyethylene (HDPE), medium density polyethylene (MDPE), low density polyethylene (LDPE), polypropylene, polyvinylchloride, polycarbonate, polytetrafluoroethylene (PFTE), polyethylene terephthalate (PET), polystyrene (PS), polymethylpentene, and other suitable foam materials.

In some aspects, the applicator 180 may further include a detachable tip overlay 118 that can, for example, fit over the applicator tip 110. The detachable tip overlay 118 preferably has a narrow distal end 112, relative to the applicator tip 110, and provides for a more limited, controlled, and precise release of the adhesive 150 and its application to the desired surface. The detachable tip overlay 118 may be comprised of a porous material, including a fibrous swab, a sponge, foam, bristles, and other suitable materials that allow an adhesive 150 to flow through it. The detachable tip overlay 118 may be comprised of any of the same suitable materials that may be used to comprise the applicator tip 110 and porous applicator tip 106. The detachable tip overlay 118, the applicator tip 110, and the porous applicator tip may, but need not be, comprised of the same material.

The detachable tip overlay 118 preferably is removably placed over top of the applicator tip 110 to allow fluid communication between the two tips and the free passage of adhesive 150 through each. The detachable tip overlay 118 may comprise a socket 116 that fits over top of the applicator tip 110 and porous applicator tip 106 allowing the overlay 118 and tip 110 to fit together, for example, with a friction fit.

The applicator body 120, including the flange 127, the grip 128, and the channel 123, may be fabricated from any suitable materials. In preferred aspects, the applicator body 120 and channel 123 is made of a material that can prevent or reduce the premature polymerization of adhesives 150 flowing through the channel 123. Suitable materials include, but are not limited to, high density polyethylene (HDPE), medium density polyethylene (MDPE), low density polyethylene (LDPE), polypropylene, polyvinylchloride, polycarbonate, polytetrafluoroethylene (PFTE), polyethylene terephthalate (PET), polystyrene (PS), and polymethylpentene. The grip 128 and the channel 123 are preferably flexible.

The container 140 may be fabricated from any suitable materials that have a desired barrier property for moisture and air so as to substantially reduce, inhibit, or prevent the premature polymerization of adhesives 150 stored therein. Suitable materials for the container 140 include, but are not limited to, high density polyethylene (HDPE), medium density polyethylene (MDPE), low density polyethylene (LDPE), polypropylene, polyvinylchloride, acrylonitrile copolymer, polycarbonate, polytetrafluoroethylene (PFTE), polyethylene terephthalate (PET), and other known moisture- and air-impermeable materials. In some preferred aspects, the container 140 is made of multi-layer sheet material comprising an acrylonitrile copolymer as the inner layer. In some other preferred aspects, the entire container 140 is made of a single, but relatively thick, layer of an acrylonitrile copolymer.

Suitable acrylonitrile copolymers used to construct the container 140 include acrylonitrile copolymers produced by polymerizing a major proportion of a monounsaturated nitrile and a minor proportion of another monovinyl monomer or indene copolymerizable nitrile polymers produced by polymerizing a major portion of a monounsaturated nitrile and a minor portion of another monovinyl monomer or indene copolymerizable therewith in the presence of a diene rubber, polyacarylates, polymethoactrylate, polyalkyl methacrylates, polyethers, polysiloxanes, polysulfones, polyphenylene sulfide, polyether ether ketones, thermoplastic polyimides, polybenzimidazoles, polyquinoxalones, polyoxazolines, styrene-acrylonitrile copolymer and acrylonitrile-butadiene-styrene copolymer, vinyl acetate containing polymers, maleic anhydride containing polymers, butadiene and/or isoprene based elastomers, acrylonitrile, and methacrylonitrile. Preferred acrylonitrile copolymers include copolymer of acrylonitrile and methyl acrylate (Barex®, BP Amoco Chemical Co. Corp., Warrenville, Ill.).

Acrylonitrile copolymers used to construct the container 140 may be used to provide high barrier properties that ensure the stability of a cyanoacrylate adhesive 150 stored therein. The exceptional barrier properties offered by acrylonitrile copolymer make it an ideal material for use in construction of the container 140 in accordance with the invention. Acrylonitrile copolymers offer a high barrier to oxygen at all levels of relative humidity. This helps ensure that a consistently high barrier to oxygen is maintained, regardless of the humidity of the surrounding environment. In addition, the water vapor barrier properties of acrylonitrile copolymer make it a desirable material for packaging and sterilizing cyanoacrylate-based adhesive materials in accordance with the invention.

The container 140 may hold any suitable volume of adhesive 150. In some aspects, the container 140 is capable of holding a volume of about 0.1 mL to about 20 mL of adhesive 150. In some preferred aspects, the container 140 is capable of holding a volume of about 0.2 mL to about 15 mL of adhesive 150, and in more preferred aspects, the container 140 is capable of holding a volume of about 0.2 mL to about 10 mL of adhesive 150. In order to inhibit the premature polymerization of the adhesive 150, the volume of the container 140 is preferably filled about 50 percent to about 80 percent, and more preferably filled about 60 percent to about 80 percent, with the adhesive 150.

The adhesive 150, in a container 140 constructed from acrylonitrile copolymer, can be sterilized by radiation sterilization such as gamma sterilization, electron beam sterilization and x-ray sterilization. The applicator 180, including all of the component parts as described or exemplified herein, is preferably compatible with these radiation sterilization techniques such that the adhesive 150 remains stable while present in the container 140 following radiation sterilization. The adhesive 150 sterilized by radiation sterilization in the applicator 180 may provide long-term shelf-life stability for a period of at least about 6 months, preferably at least about 12 months, and more preferably at least about 24 months. Shelf-life stability relates, in part, to the adhesive remaining substantially unpolymerized for the specified period of time following exposure to radiation, including remaining substantially unpolymerized while stored at or about room temperature, and at about 30% to about 60% humidity, about 40% to about 50% humidity, or less than about 50% humidity for the specified period of time.

Figure 4:
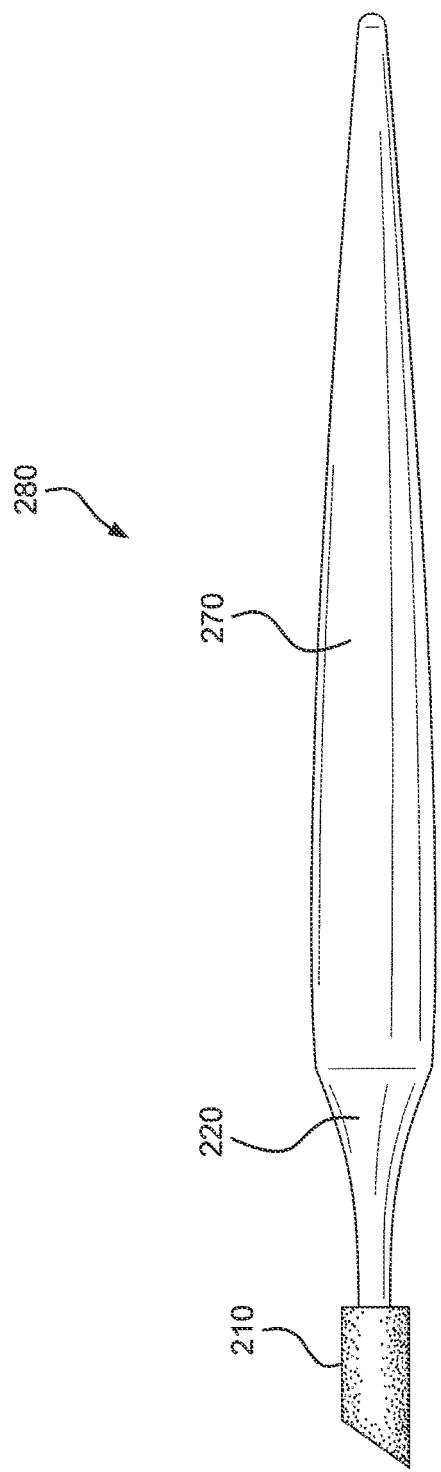
FIG. 4 is a perspective view of a second exemplary applicator of this invention.
Figure 5:
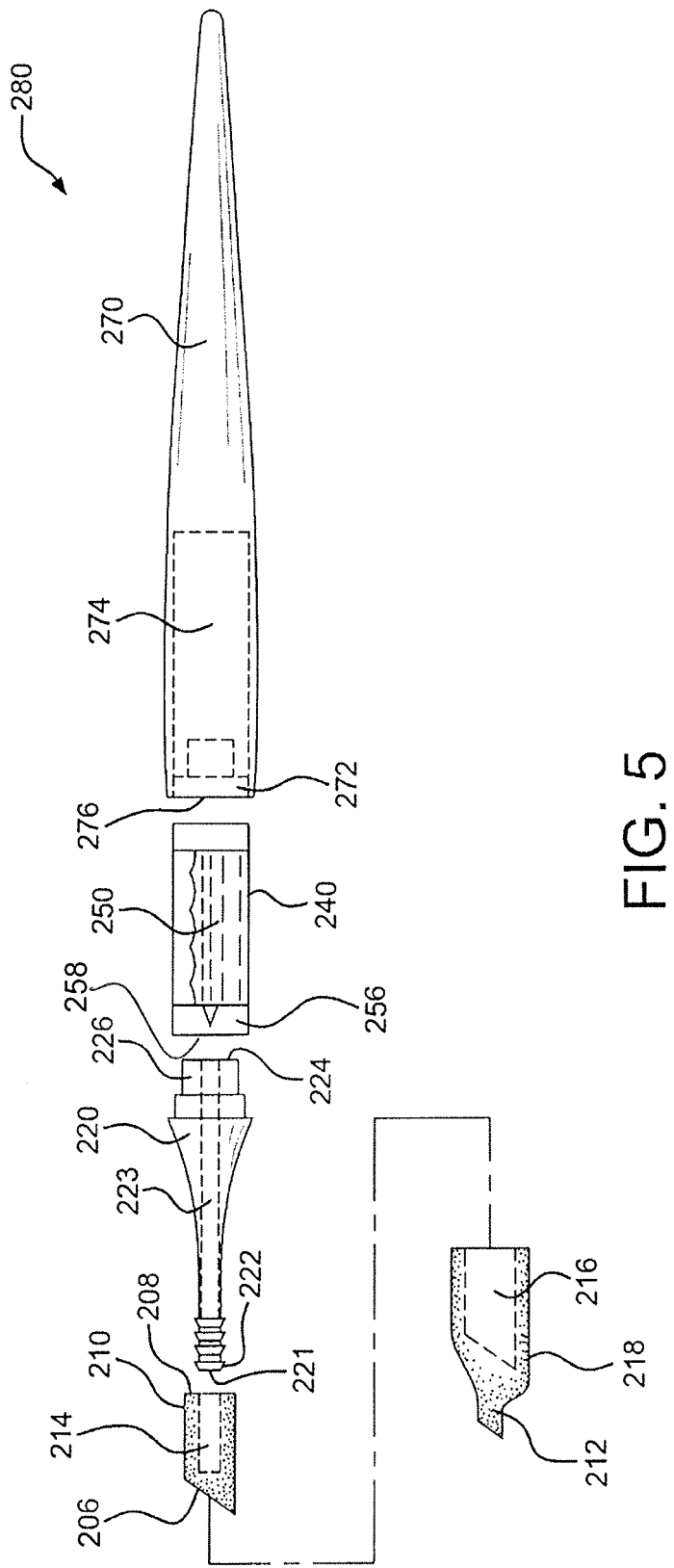
FIG. 5 is an exploded view of the exemplary embodiment of FIG. 4.
Figure 6:
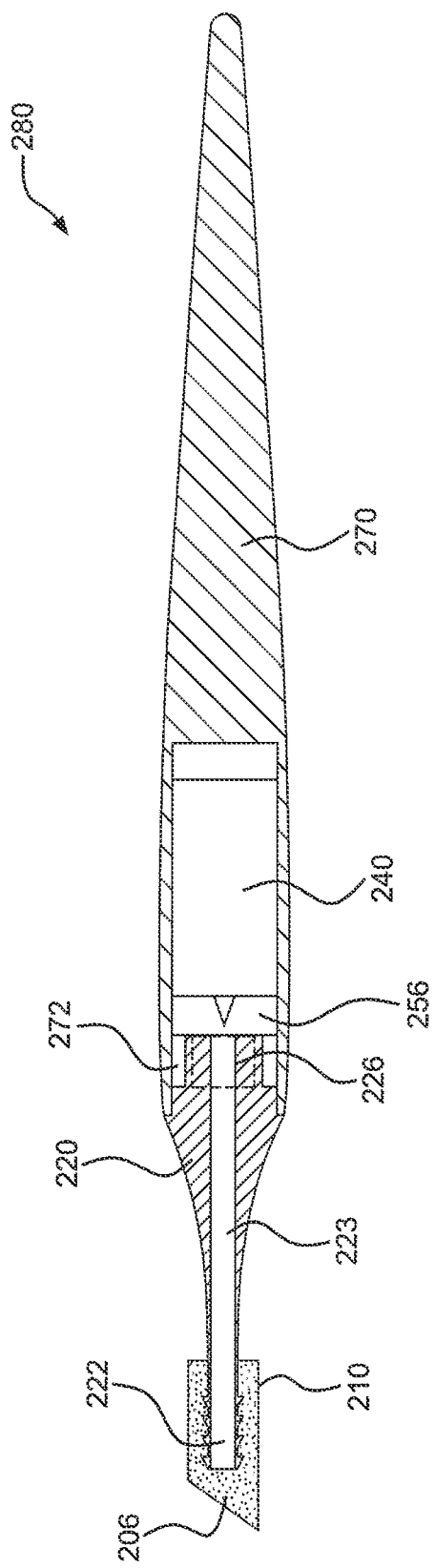
FIG. 6 is a cross-sectional view of the exemplary embodiment of FIG. 4.

FIGS. 4-6 show a perspective view, an exploded view and a cross-sectional view, respectively, of a second embodiment of the applicator of the invention. In some aspects, an applicator 280 comprises the following basic components: an applicator tip 210, a body 220, and a handle 270. The handle 270 may, for example, include a housing 274 for holding a removable adhesive container 240.

The removable adhesive container 240 may comprise a packet or a pouch, for example, a stick pack, and may comprise a frangible seal 256 at its distal end 258, which may be in communication with or attach to a channel 223 in the body 220, as shown in the cross-sectional view in FIG. 6. The adhesive container 240 preferably contains and stores an adhesive 250.

The body 220 may be connected to the handle 270 using the male portion of a luer lock 226 on the proximal end 224 of the body 220 and the female portion of a luer lock 272 on the distal end 276 of the handle 270. The body 220 and the handle 270 preferably fit together in a tight connection in order to prevent leakage of an adhesive 250 from the junction between the body 220 and the handle 270. The body 220 also has a distal end 222, which may connect with an applicator tip 210 at the proximal end 208 of the applicator tip 210, for example, by fitting inside of a socket 214 in the tip 210. The body 220 and the applicator tip 210 may fit together using any suitable connection, including a snap-fit connection, a friction-fit connection, or a screw cap connection. The applicator tip 210 and the body 220 preferably fit together in a tight connection in order to prevent leakage of an adhesive 250 from the junction between the tip 210 and the body 220.

The handle 270 may comprise a female luer lock portion 272 at the distal end 276, and a housing 274 for containing or storing a removable adhesive container 240. The adhesive container 240 may, for example, friction fit within the housing 274. In some aspects, the adhesive container 240 may comprise a frangible seal 256, which can be opened, for example, by puncturing, bending, breaking, or pressing such that the adhesive 250 may be released from the container 240 and begin to flow through the applicator 280.

For example, the applicator 280 may be activated when the handle 270 of the applicator 280 is squeezed inward or bent, for example, where the adhesive container 240 is located. Upon the application of pressure or bending motion to the handle 270, and with it the adhesive container 240 housed therein, the frangible seal 256 on the container 240 is compromised such that the adhesive 250 contained within the container 240 flows out of the container 240, into the channel 223 at the proximal end 224 of the body 220, through the channel 223, out from the channel opening 221 at the distal end, into the applicator tip 210, and out from a porous applicator tip 206, which upon exiting the porous applicator tip 206 may be applied to a desired surface.

The body 220 and/or handle 270 may be constructed from any suitable materials. For example, the body 220 and/or the handle 270 is preferably made of a material that can substantially reduce, inhibit, or prevent the premature polymerization of adhesives. Suitable materials for the applicator body include, but are not limited to, high density polyethylene (HDPE), medium density polyethylene (MDPE), low density polyethylene (LDPE), polypropylene, polyvinylchloride, polycarbonate, polytetrafluoroethylene (PFTE), polyethylene terephthalate (PET), polystyrene (PS), and polymethylpentene.

The applicator tip 210, allows the adhesive 250 to be applied to a desired surface, for example, skin, in a controlled manner. The tip 210, including the porous applicator tip 206, may be comprised of a porous material, including a fibrous swab, a sponge, foam, bristles, and other suitable materials that allow an adhesive 250 to flow through the tip 210. The applicator tip 210, including the porous applicator tip 206, may be fabricated from any suitable materials, including but not limited to foams, rubber, plastics, thermosets, films, cotton, alginate, or membranes. The foam material may be, but is not limited to, polyolefin foam, polyether polyurethane foam, polyester polyurethane foam, high density polyethylene (HDPE), medium density polyethylene (MDPE), low density polyethylene (LDPE), polypropylene, polyvinylchloride, polycarbonate, polytetrafluoroethylene (PFTE), polyethylene terephthalate (PET), polystyrene (PS), polymethylpentene, and other suitable foam materials.

In some aspects, the applicator 280 may further include a detachable tip overlay 218 that can, for example, fit over the applicator tip 210. The detachable tip overlay 218 preferably has a narrower distal end 212, relative to the distal end of the applicator tip 210, and provides for a more limited, controlled, and precise release of the adhesive 250 and its application to the desired surface. The detachable tip overlay 218 may be comprised of a porous material, including a fibrous swab, a sponge, foam, bristles, and other suitable materials that allow an adhesive 250 to flow through it. The detachable tip overlay 218 may be comprised of any of the same suitable materials that may be used to comprise the applicator tip 210 and porous applicator tip 206. The detachable tip overlay 218, the applicator tip 210, and the porous applicator tip may, but need not be, comprised of the same material.

The detachable tip overlay 218 preferably is removably placed over top of the applicator tip 210 to allow fluid communication between the two tips and the free passage of adhesive 250 through each. The detachable tip overlay 218 may comprise a socket 216 that fits over top of the applicator tip 210 and porous applicator tip 206 allowing the overlay 218 and tip 210 to fit together, for example, with a friction fit.

The handle 270 is preferably configured to facilitate compromise of the adhesive container 240, and to allow the user to effectively control the flow rate of the adhesive 250 out from the applicator 280 and on to the surface. For example, in some aspects, a user may apply pressure to, squeeze, or bend the handle 270 to compromise the adhesive container 240 or its frangible seal 256 so that the adhesive 250 can be released from the container 240. Thus, the handle 270 is preferably flexible, at least at the location where the container 240 is housed. The handle 270 can be held just like a pen or brush between the user's thumb and one or more fingers such that the user can ergonomically hold and utilize the applicator 280 when applying adhesive 250.

The flow rate of the adhesive 250 through the applicator 280 may be controlled, for example, by the user providing inward pressure on the handle 270 or the body 220. The applied pressure may slow the flow of adhesive 250 out from the container 240 and into the body 220 channel 223, and ultimately, into and out from the tip 210. Pressure may also be used to constrict the channel 223, thereby slowing the rate of flow through the channel 223. In some embodiments, a desired amount of adhesive 250 can be dispensed by applying the desired level of controlling pressure to the handle 270 and/or to the body 220. The handle 270 and/or the body 220 is therefore preferably made of a flexible or semi-rigid material in order to permit the user to compress the handle 270 or the body 220 inward and control the flow of the adhesive 250 to the application site. Suitable materials include, but are not limited to, rubber, thermoplastics, thermosets, high density polyethylene (HDPE), medium density polyethylene (MDPE), low density polyethylene (LDPE), polypropylene, or polyesters.

The adhesive container 240 may be constructed from any suitable materials that have a desired barrier property for moisture and air so as to substantially reduce, inhibit, or prevent premature polymerization of adhesive 250 stored inside of the container 240 until the container 240 is compromised. Suitable materials for the container 240 include, but are not limited to, acrylonitrile copolymer, high density polyethylene (HDPE), medium density polyethylene (MDPE), low density polyethylene (LDPE), polypropylene, polyvinylchloride, polycarbonate, polytetrafluoroethylene (PFTE), and polyethylene terephthalate (PET), and other similar polymeric materials.

In some preferred embodiments, the container 240 may be comprised of a multi-layer sheet material with acrylonitrile copolymer making up the inner layer. In some preferred embodiments, the container 240 is comprised of a single and thick layer of an acrylonitrile copolymer. Suitable acrylonitrile copolymers used to construct the container 240 include acrylonitrile copolymers produced by polymerizing a major proportion of a monounsaturated nitrile and a minor proportion of another monovinyl monomer or indene copolymerizable nitrile polymers produced by polymerizing a major portion of a monounsaturated nitrile and a minor portion of another monovinyl monomer or indene copolymerizable therewith in the presence of a diene rubber, polyacarylates, polymethoactrylate, polyalkyl methacrylates, polyethers, polysiloxanes, polysulfones, polyphenylene sulfide, polyether ether ketones, thermoplastic polyimides, polybenzimidazoles, polyquinoxalones, polyoxazolines, styrene-acrylonitrile copolymer and acrylonitrile-butadiene-styrene copolymer, vinyl acetate containing polymers, maleic anhydride containing polymers, butadiene and/or isoprene based elastomers, acrylonitrile, and methacrylonitrile. Preferred acrylonitrile copolymers include copolymer of acrylonitrile and methyl acrylate (Barex®, BP Amoco Chemical Co. Corp., Warrenville, Ill.).

The volume of the applicator container 240 may range from about 0.1 mL to about 20 mL, preferably about 0.2 mL to about 15 mL, and more preferably about 0.2 mL to about 10 mL. In order to inhibit the premature polymerization of the adhesive 250, the volume of the container 240 is preferably filled about 50 percent to about 80 percent and more preferably filled about 60 percent to about 80 percent, with the adhesive 250.

In some embodiments, the frangible seal 256 located on the container 240 provides a desired barrier property for moisture and air in order to substantially reduce, inhibit, or prevent premature polymerization of, and maintain the stability of the adhesive 250 when the adhesive is sterilized or stored in the container 240. The frangible seal 256 is preferably constructed of particular materials and in such a way that allows it to be readily compromised by bending motion or pressure in order to release the adhesive 250. Suitable materials for the frangible seal 256 may include, but are not limited to, aluminum foil, plastic membrane, laminated aluminum foil, plastic wrap, waxed paper, oiled paper, or other suitable packaging material. Laminated aluminum foil is preferred, and may be composed of at least two layers of different materials which include, but are not limited to, aluminum, acrylonitrile copolymer, low density polyethylene, low density polypropylene, or polyethylene teraphthalate. In a more preferred embodiment, laminated aluminum foil with acrylonitrile copolymer as the inner layer is used to construct the frangible foil 256.

The acrylonitrile copolymer adhesive 250 in the container 240 can be sterilized by radiation sterilization, such as gamma sterilization, electron beam sterilization and x-ray sterilization. The applicator 280 is also constructed of materials compatible with radiation sterilization techniques such that the applicator 280 housing a container 240 with an adhesive 250 can be sterilized via radiation without inducing curing of the adhesive 250. An adhesive 250 sterilized by radiation sterilization while in the applicator 280 may therefore provide a long-term shelf-life stability of at least about 6 months, preferably at least about 12 months, and more preferably at least about 24 months. Shelf-life stability relates, in part, to the adhesive remaining substantially unpolymerized for the specified period of time following exposure to radiation, including remaining substantially unpolymerized while stored at or about room temperature, and at about 30% to about 60% humidity, about 40% to about 50% humidity, or less than about 50% humidity for the specified period of time.

Figure 8:
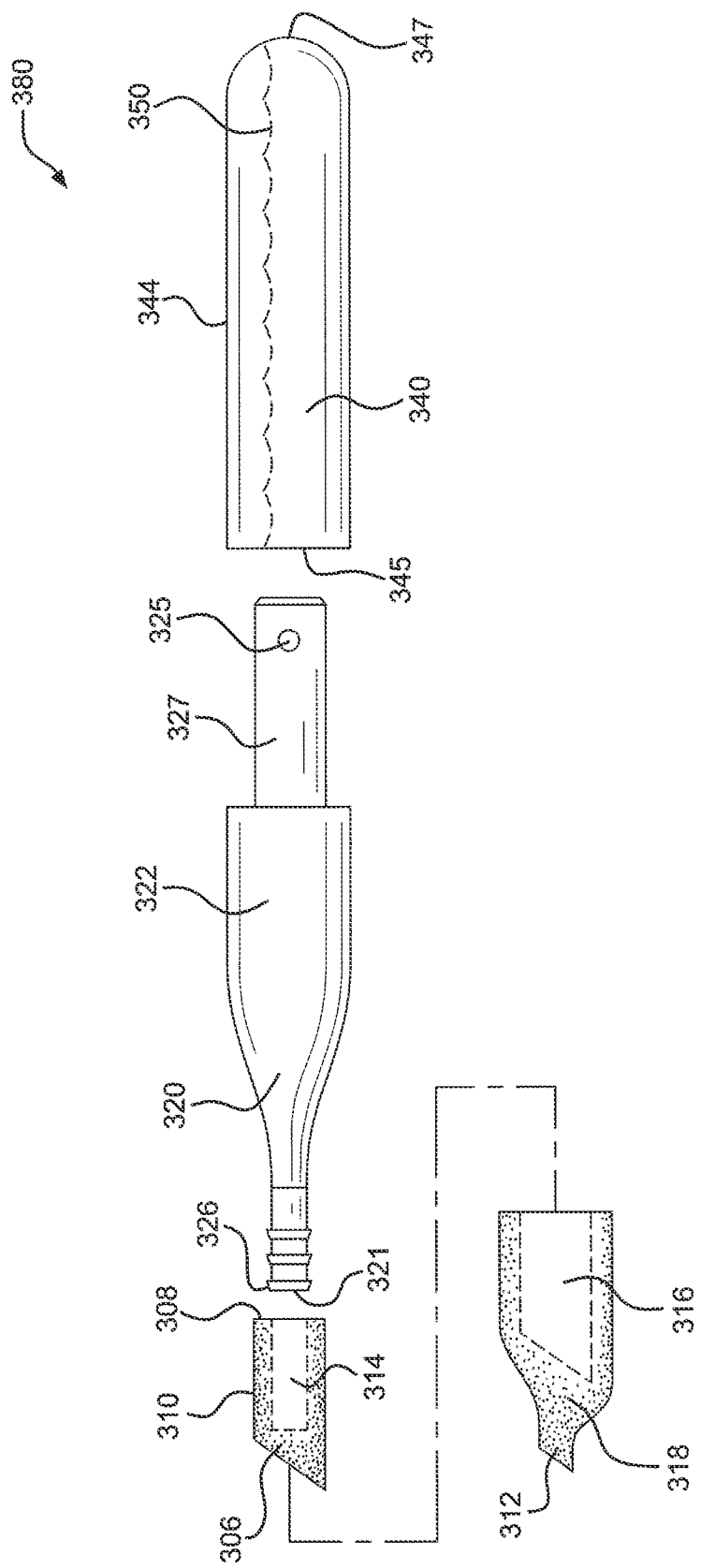
FIG. 8 is an exploded view of the exemplary embodiment of FIG. 7A-C.
Figure 9:
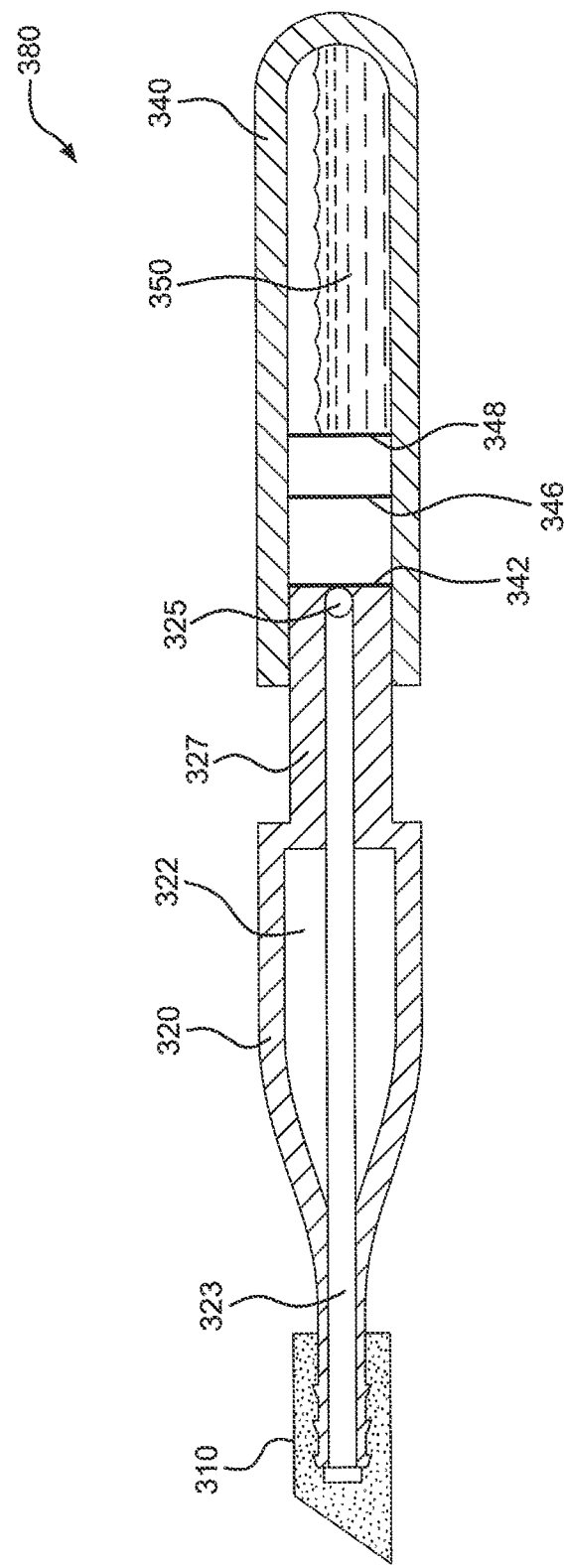
FIG. 9 is a cross-sectional view of the exemplary embodiment of FIG. 7A-C.

FIGS. 7-9 illustrate a perspective view, an exploded view and a cross-sectional view, respectively, of a third embodiment of the applicator of the invention. As shown in FIG. 7, an applicator 380 according to this embodiment includes these basic components: an applicator tip 310, an applicator body 320, and a container 340. The container 340 is movable relative to the body 320, for example, by being compressed together. Optionally, a lock 330 may be placed between the applicator body 320 and the container 340.

In some aspects, the applicator body 320 comprises a distal end 326, a reservoir 322, a flange 327 which is equipped with a hole 325 and a channel 323, as shown in FIGS. 8 and 9. The hole 325 and the channel 323 are in communication for allowing an adhesive 350 to flow out from the container 340 and through the body 320 of the applicator 380.

The flange 327 of the applicator body 320 may be inserted into the distal end 345 of the container 340, for example, via a friction fit, and sealed tightly with a distal seal 342. The connection between the applicator body 320 and the container 340 is preferably configured in a way to prevent the applicator 380 from accidental activation, which could induce premature curing of the adhesive 350 stored in the container 340. For example, a lock 330 can be optionally placed between the applicator body 320 and the container 340 to prevent the body 320 and the container 340 from being pushed together.

To activate the applicator 380 and start the flow of adhesive 350 through the applicator 380, a user may first remove the lock 330, if the lock is present. In the absence of the lock 330, the user may press the container 340 and the body 320 together, for example, by applying pressure to the proximal end 347 of the container 340. As the container 340 is pressed together with the body 320, the flange 327 penetrates and passes through the middle seal 346 and the proximal seal 348, and moves into the container 340, thereby providing the hole 325 with access to adhesive 350 stored in the container 340. The adhesive 350 can then flow through the hole 325, and into the channel 323, out from an opening 321 in the distal end 326 of the body 320 and into the tip 310.

The container 340 comprises a plurality of walls 344 that define a chamber 349 that is preferably open at the distal end 345, which may be closed off by a plurality of seals, for example, a distal seal 342, a middle seal 346, and a proximal seal 348 such as those shown in the FIGS. 8 and 9. The walls 344 container 340 include a wall 344 at the proximal end 347, which may comprise a round shape.

When the applicator 380 is in a locked mode, the hole 325 is positioned between the distal seal 342 and the middle seal 346 so that the hole 325 has no access to the adhesive 350 in the container 340. When a pressure is applied to the proximal end 347 wall 344 of the container 340 to activate the applicator 380, or optionally, when the lock 330, if present, is removed, the container 340 can be moved toward the applicator body 320. As the container 340 and body 320 are compressed together, the flange 327, and with it the hole 325, can penetrate and pass through the middle seal 346 and the proximal seal 348 such that the hole 325 is in communication with adhesive 350 stored in the container 340. The adhesive 350 can then pass through the hole 325 and into the channel 323 of the body 320.

The distal end 326 of the applicator body 320 attaches to the proximal end 308 of the applicator tip 310. For example, the body 320 and the tip can fit together with a friction-fit, a snap-fit, or a screw-fit. The distal end 326 of the body 320 may fit inside of the proximal end 308 of the tip, for example, via a socket 314 in the tip 310. The connection between the applicator tip 310 and the applicator body 320, including the socket 314, is preferably sufficiently tight in order to prevent leakage of the adhesive 350 out from the junction of the body 320 and the tip 310 during use of the applicator 380.

In some aspects, the applicator 380 may further include a detachable tip overlay 318 that can, for example, fit over the applicator tip 310. The detachable tip overlay 318 preferably has a narrower distal end 312, relative to the distal end of the applicator tip 310, and provides for a more limited, controlled, and precise release of the adhesive 350 and its application to the desired surface. The detachable tip overlay 318 may be comprised of a porous material, including a fibrous swab, a sponge, foam, bristles, and other suitable materials that allow an adhesive 350 to flow through it. The detachable tip overlay 318 may be comprised of any of the same suitable materials that may be used to comprise the applicator tip 310. The detachable tip overlay 318, the applicator tip 310, and the porous applicator tip 306 may, but need not be, comprised of the same material.

The detachable tip overlay 318 preferably is removably placed over top of the applicator tip 310 to allow fluid communication between the two tips and the free passage of adhesive 350 through each. The detachable tip overlay 318 may comprise a socket 316 that fits over top of the applicator tip 310 and porous applicator tip 306 allowing the overlay 318 and tip 310 to fit together, for example, with a friction fit.

The applicator tip 310, including the porous applicator tip 306, and the detachable tip overlay 318 may be comprised of a porous material, including a fibrous swab, a sponge, foam, bristles, and other suitable materials that allow the adhesive 350 to flow through the tip 310 and the porous applicator tip 306 or overlay 318. The applicator tip 310, porous applicator tip 306, or tip overlay 318 may be fabricated from any suitable materials, including but not limited to foams, rubber, plastics, thermosets, films, cotton, alginate, or membranes. The foam material may be, but is not limited to, polyolefin foam, polyether polyurethane foam, polyester polyurethane foam, high density polyethylene (HDPE), medium density polyethylene (MDPE), low density polyethylene (LDPE), polypropylene, polyvinylchloride, polycarbonate, polytetrafluoroethylene (PFTE), polyethylene terephthalate (PET), polystyrene (PS), polymethylpentene, and other suitable foam materials.

The container 340 may be constructed from any suitable materials that provide a barrier to moisture and air so that the premature polymerization of adhesive 350 can be substantially reduced, inhibited, or prevented. Suitable materials include, but are not limited to, high density polyethylene (HDPE), medium density polyethylene (MDPE), low density polyethylene (LDPE), polypropylene, polyvinylchloride, acrylonitrile copolymer, polycarbonate, polytetrafluoroethylene (PFTE), and polyethylene terephthalate (PET), and other polymeric materials that provide a moisture and air barrier.

In some preferred aspects, the container 340 comprises a single, thick layer of acrylonitrile copolymer. In some preferred aspects, the container 340 comprises a plurality of layers, with an acrylonitrile copolymer inner layer. Suitable acrylonitrile copolymers used to construct the container 340 include acrylonitrile copolymers produced by polymerizing a major proportion of a monounsaturated nitrile and a minor proportion of another monovinyl monomer or indene copolymerizable nitrile polymers produced by polymerizing a major portion of a monounsaturated nitrile and a minor portion of another monovinyl monomer or indene copolymerizable therewith in the presence of a diene rubber, polyacrylates, polymethoactrylate, polyalkyl methacrylates, polyethers, polysiloxanes, polysulfones, polyphenylene sulfide, polyether ether ketones, thermoplastic polyimides, polybenzimidazoles, polyquinoxalones, polyoxazolines, styrene-acrylonitrile copolymer and acrylonitrile-butadiene-styrene copolymer, vinyl acetate containing polymers, maleic anhydride containing polymers, butadiene and/or isoprene based elastomers, acrylonitrile, and methacrylonitrile. Preferred acrylonitrile copolymers include copolymer of acrylonitrile and methyl acrylate (Barex®, BP Amoco Chemical Co. Corp., Warrenville, Ill.).

The volume of the container 340 may range from about 0.1 mL to about 20 mL, preferably about 0.2 mL to about 15 mL, and more preferably about 0.2 mL to about 10 mL. In order to inhibit the premature polymerization of the adhesive 350, the volume of the container 340 is preferably filled about 50 percent to about 80 percent and more preferably filled about 60 percent to about 80 percent, with the adhesive 350.

The applicator body 320, including the reservoir 322, the flange 327, and the channel 323, may be constructed from any suitable material. In some preferred aspects, the applicator body 320 may be made of a material that suitable for substantially reducing, inhibiting, or preventing the premature polymerization of an adhesive 350. Suitable materials for the applicator body 320 include, but are not limited to, high density polyethylene (HDPE), medium density polyethylene (MDPE), low density polyethylene (LDPE), polypropylene, polyvinylchloride, polycarbonate, polytetrafluoroethylene (PFTE), polyethylene terephthalate (PET), polystyrene (PS), and polymethylpentene.

The distal seal 342, middle seal 346, and proximal seal 348 may be comprise of any suitable material that may be readily penetrated by the flange 327 during activation of the application 380, while maintaining a sufficient seal for container 340 to prevent leakage of the adhesive 350 once the seals 342, 346, and 348 have been compromised by the flange 327.

The applicator 380 is compatible with radiation sterilization such as gamma sterilization, electron beam sterilization and x-ray sterilization. The adhesive 350 stored in the applicator 380 can be sterilized by radiation sterilization, without initiation of curing upon sterilization. In a more preferred embodiment, the adhesive 350 sterilized by radiation sterilization technique in the applicator 380 may provide long term shelf life stability of at least about 6 months, preferably at least about 12 months and more preferably at least about 24 months. Shelf-life stability relates, in part, to the adhesive remaining substantially unpolymerized for the specified period of time following exposure to radiation, including remaining substantially unpolymerized while stored at or about room temperature, and at about 30% to about 60% humidity, about 40% to about 50% humidity, or less than about 50% humidity for the specified period of time.

Figure 10:
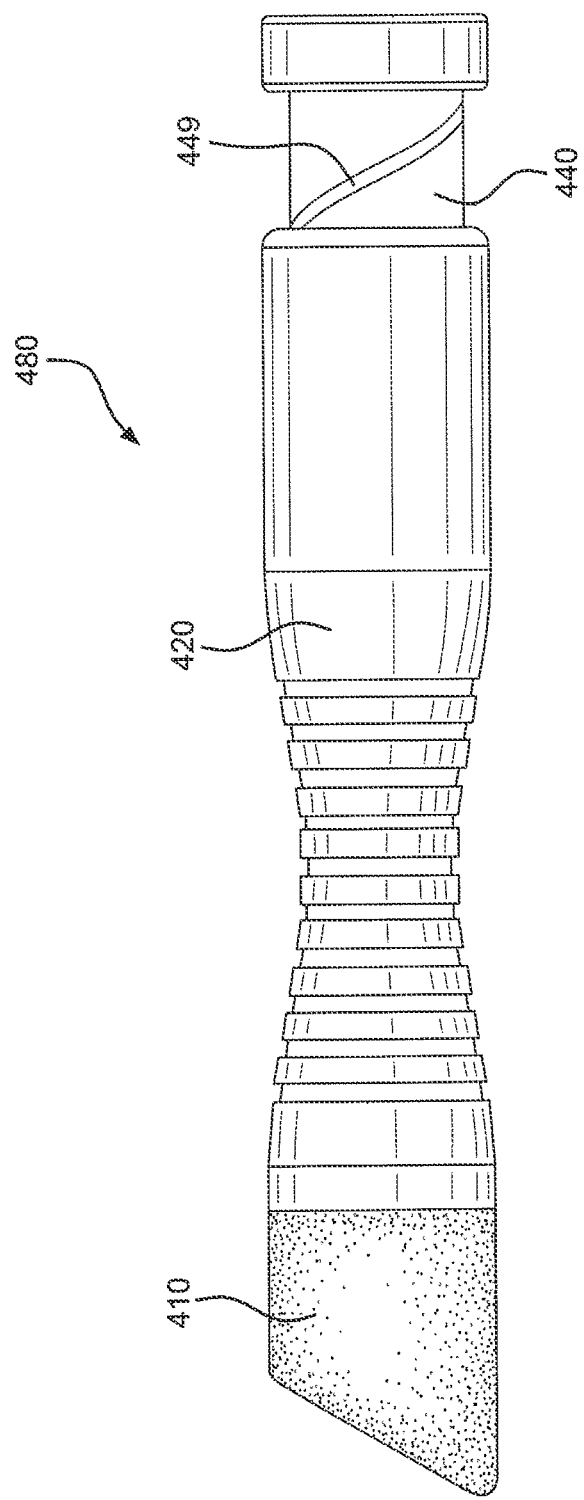
FIG. 10 is a perspective view of a fourth exemplary applicator of this invention.
Figure 11:
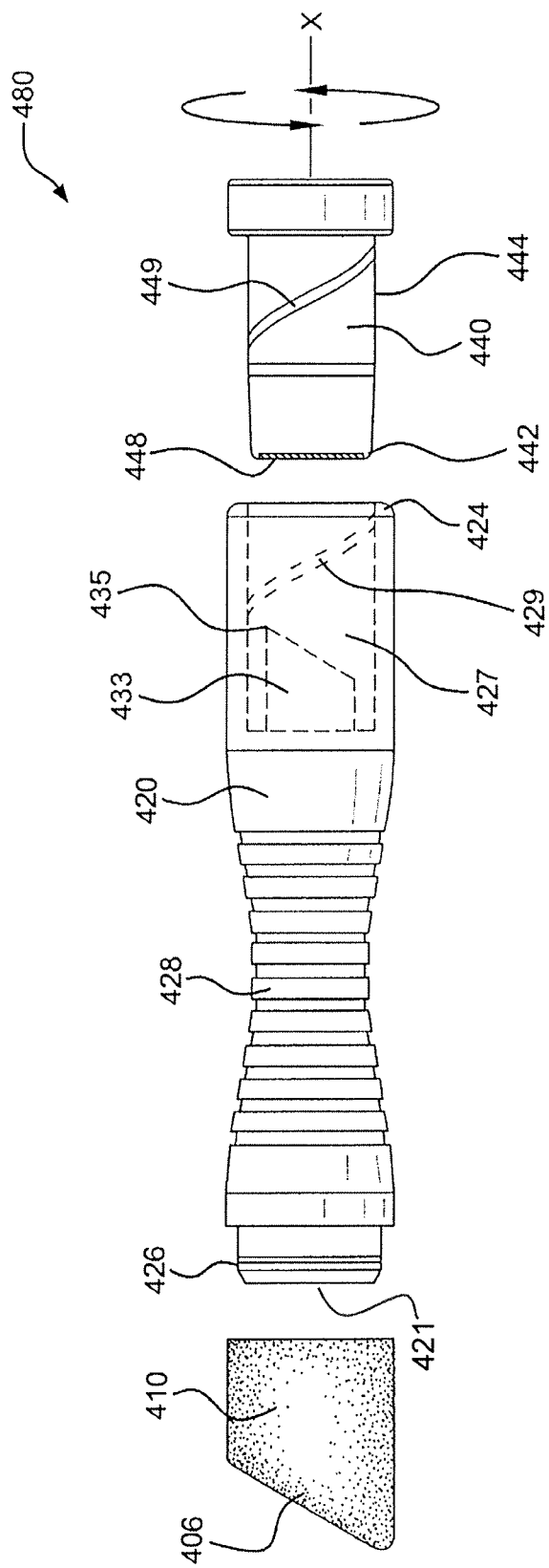
FIG. 11 is an exploded view of the exemplary embodiment of FIG. 10.
Figure 12:
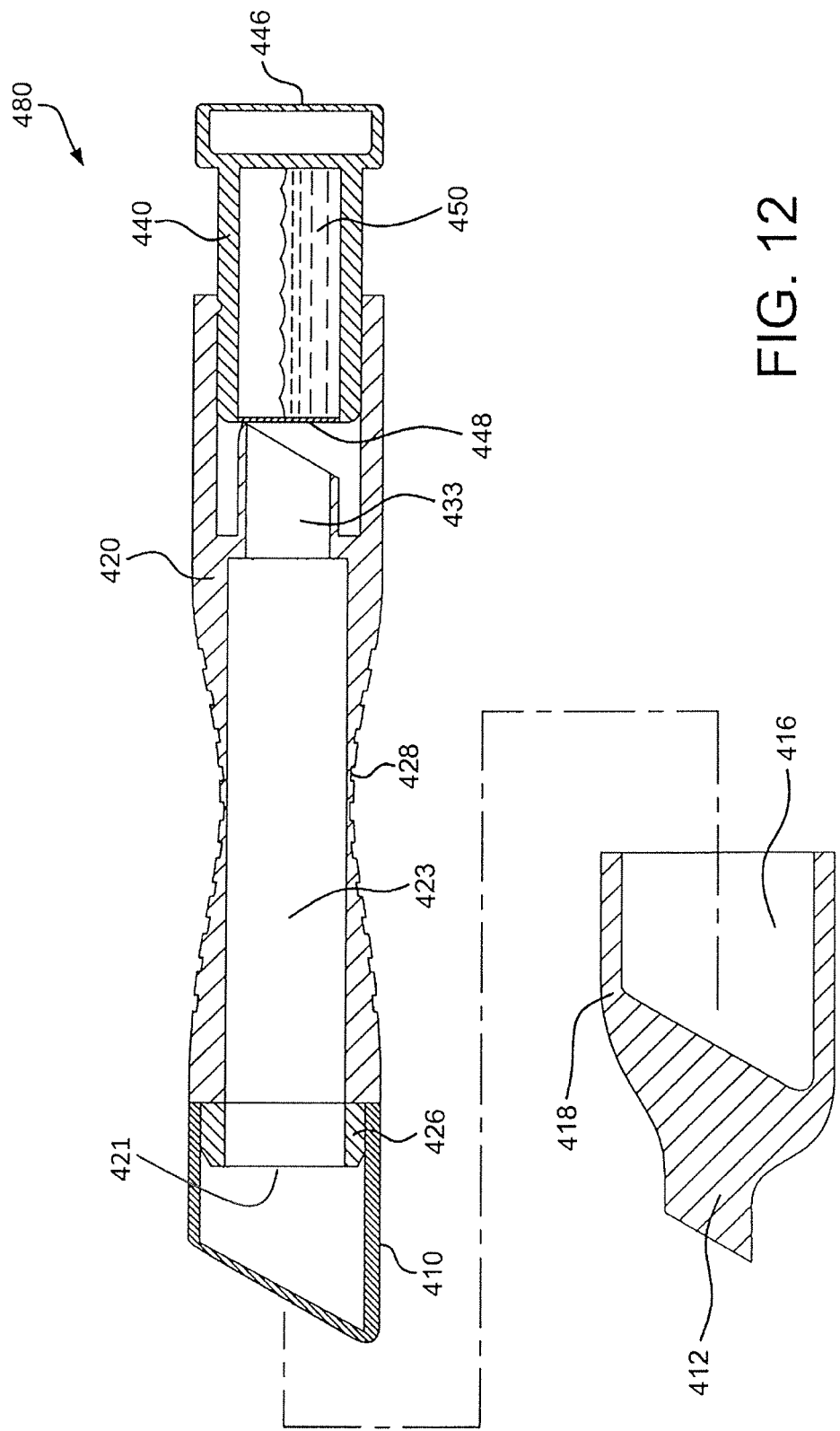
FIG. 12 is a cross-sectional view of the exemplary embodiment of FIG. 10.

FIGS. 10-12 represent a perspective view, an exploded view, and a cross-sectional view, respectively, of a fourth non-limiting embodiment of an applicator of the invention. An applicator 480 comprises an applicator tip 410, an applicator body 420, and a container 440. The container 440 is rotatable relative to the applicator body 420, with the rotation mediated, for example, by screw threads 449 present on the external surface of the walls 444 container 440 and matching screw threads 429 present on the surface of the walls of a cavity 427 in the body 420. In some aspects, the applicator 480 is activated by a user rotating the container 440 about an axis x, whereupon the applicator body 420 and container 440 are moved together.

The cavity 427 of the applicator body 420 includes at least one projection 433 extending proximally, and toward the container 440. The projection 433, may comprise one or more points on its tip 435, and/or may comprise one or more blades on the tip 435. The projection 433 functions, for example, to compromise the integrity of a seal 448 present over an open distal end 442 of the container 440. Thus, as a user rotates the container 440 about the axis x and the container 440 moves closer to the body 420, the projection 433 penetrates, cuts, or otherwise compromises the seal 448 on the container 440, and an adhesive 450 stored inside the container 440 is released into the applicator body 420, and may be released into a channel 423 that passes through the applicator body 420. The adhesive 450 passes through the applicator body 420, and out through an opening 421 at the distal end 426 end of the applicator body 420, and into the applicator tip 410. As the adhesive 450 exits the applicator tip 410, the user may apply the adhesive 450 to a desired surface.

A grip 428 on the applicator body 420 allows a user to conveniently hold and position the applicator 480 during use. For example, a user may hold the grip 428 similar to how a pen is held, between the thumb and one or more fingers. The grip 428 may itself be comprised of a flexible material that allows the user to squeeze the grip 428 inward. Constricting the grip 428 may constrict the body 420 or channel 423 in order to control the flow of the adhesive 450 through the body 420 or channel 423. The flow rate of adhesive 450 may be controlled, for example, by the user providing a desired amount of pressure on the grip 428 of the body 420. A desired amount of adhesive 450 can thus be dispensed by applying a desired amount of force to the grip 428.

The applicator tip 410 may be connected to the distal end 426 of the applicator body 420 with any suitable connection, such as a friction fit, a Luer lock, a screw cap, or a snap-fit. The applicator tip 410 preferably fits tightly into the distal end 426 of the applicator body 420 to substantially reduce, inhibit, or prevent any leakage of adhesive 450 flowing through the applicator 480 from this junction. The applicator tip 410 may comprise a porous applicator tip 406 at the distal end 412. The applicator tip 410, including the porous applicator tip 406, allows the adhesive 450 to be applied to a desired surface, for example, skin, in a controlled manner.

The tip 410, including the porous applicator tip 406, may be comprised of a porous material, including a fibrous swab, a sponge, foam, bristles, and other suitable materials that allow an adhesive 450 to flow through the tip 410 and/or porous applicator tip 406. The applicator tip 410, including the porous applicator tip 406, may be fabricated from any suitable materials, including but not limited to foams, rubber, plastics, thermosets, films, cotton, alginate, or membranes. The foam material may be, but is not limited to, polyolefin foam, polyether polyurethane foam, polyester polyurethane foam, high density polyethylene (HDPE), medium density polyethylene (MDPE), low density polyethylene (LDPE), polypropylene, polyvinylchloride, polycarbonate, polytetrafluoroethylene (PFTE), polyethylene terephthalate (PET), polystyrene (PS), polymethylpentene, and other suitable foam materials.

In some aspects, the applicator 480 may further include a detachable tip overlay 418 that can, for example, fit over the applicator tip 410. The detachable tip overlay 418 preferably has a narrow distal end 412, relative to the applicator tip 410, and provides for a more limited, controlled, and precise release of the adhesive 450 and its application to the desired surface. The detachable tip overlay 418 may be comprised of a porous material, including a fibrous swab, a sponge, foam, bristles, and other suitable materials that allow an adhesive 450 to flow through it. The detachable tip overlay 418 may be comprised of any of the same suitable materials that may be used to comprise the applicator tip 410 and porous applicator tip 406. The detachable tip overlay 418, the applicator tip 410, and the porous applicator tip may, but need not be, comprised of the same material.

The detachable tip overlay 418 preferably is removably placed over top of the applicator tip 410 to allow fluid communication between the two tips and the free passage of adhesive 450 through each. The detachable tip overlay 418 may comprise a socket 416 that fits over top of the applicator tip 410 and porous applicator tip 406 allowing the overlay 418 and tip 410 to fit together, for example, with a friction fit.

The container 440 may be fabricated from any suitable materials that have a desired barrier property for moisture and air so as to substantially reduce, inhibit, or prevent the premature polymerization of adhesives 450 stored therein. Suitable materials for the container 440 include, but are not limited to, high density polyethylene (HDPE), medium density polyethylene (MDPE), low density polyethylene (LDPE), polypropylene, polyvinylchloride, acrylonitrile copolymer, polycarbonate, polytetrafluoroethylene (PFTE), polyethylene terephthalate (PET), and other known moisture- and air-impermeable materials. In some preferred aspects, the container 440 is made of multi-layer sheet material comprising an acrylonitrile copolymer as the inner layer. In some other preferred aspects, the entire container 440 is made of a single, but relatively thick, layer of an acrylonitrile copolymer.

Suitable acrylonitrile copolymers used to construct the container 440 include acrylonitrile copolymers produced by polymerizing a major proportion of a monounsaturated nitrile and a minor proportion of another monovinyl monomer or indene copolymerizable nitrile polymers produced by polymerizing a major portion of a monounsaturated nitrile and a minor portion of another monovinyl monomer or indene copolymerizable therewith in the presence of a diene rubber, polyacarylates, polymethoactrylate, polyalkyl methacrylates, polyethers, polysiloxanes, polysulfones, polyphenylene sulfide, polyether ether ketones, thermoplastic polyimides, polybenzimidazoles, polyquinoxalones, polyoxazolines, styrene-acrylonitrile copolymer and acrylonitrile-butadiene-styrene copolymer, vinyl acetate containing polymers, maleic anhydride containing polymers, butadiene and/or isoprene based elastomers, acrylonitrile, and methacrylonitrile. Preferred acrylonitrile copolymers include copolymer of acrylonitrile and methyl acrylate (Barex®, BP Amoco Chemical Co. Corp., Warrenville, Ill.).

Acrylonitrile copolymers used to construct the container 440 may be used to provide high barrier properties that ensure the stability of a cyanoacrylate adhesive 450 stored therein. The exceptional barrier properties offered by acrylonitrile copolymer make it an ideal material for use in construction of the container 440 in accordance with the invention. Acrylonitrile copolymers offer a high barrier to oxygen at all levels of relative humidity. This helps ensure that a consistently high barrier to oxygen is maintained, regardless of the humidity of the surrounding environment. In addition, the water vapor barrier properties of acrylonitrile copolymer make it a desirable material for packaging and sterilizing cyanoacrylate-based adhesive materials in accordance with the invention.

The container 440 may hold any suitable volume of adhesive 450. In some aspects, the container 440 is capable of holding a volume of about 0.1 mL to about 20 mL of adhesive 450. In some preferred aspects, the container 440 is capable of holding a volume of about 0.2 mL to about 15 mL of adhesive 450, and in more preferred aspects, the container 440 is capable of holding a volume of about 0.2 mL to about 10 mL of adhesive 450. In order to inhibit the premature polymerization of the adhesive 450, the volume of the container 440 is preferably filled about 50 percent to about 80 percent, and more preferably filled about 60 percent to about 80 percent, with the adhesive 450.

The adhesive 450, in a container 440 constructed from acrylonitrile copolymer, can be sterilized by radiation sterilization such as gamma sterilization, electron beam sterilization and x-ray sterilization. The applicator 480, including all of the component parts as described or exemplified herein, is preferably compatible with these radiation sterilization techniques such that the adhesive 450 remains stable while present in the container 440 following radiation sterilization. The adhesive 450 sterilized by radiation sterilization in the applicator 480 may provide long-term shelf-life stability for a period of at least about 6 months, preferably at least about 12 months, and more preferably at least about 24 months. Shelf-life stability relates, in part, to the adhesive remaining substantially unpolymerized for the specified period of time following exposure to radiation, including remaining substantially unpolymerized while stored at or about room temperature, and at about 30% to about 60% humidity, about 40% to about 50% humidity, or less than about 50% humidity for the specified period of time.

The applicator body 420, including the projection 433, the channel 423, the cavity 427, and the screw threads 429 may be fabricated from any suitable materials. In preferred aspects, the applicator body 420 and/or channel 423 is made of a material that can prevent or reduce the premature polymerization of adhesives 450 flowing through the body 420 or channel 423. Suitable materials include, but are not limited to, high density polyethylene (HDPE), medium density polyethylene (MDPE), low density polyethylene (LDPE), polypropylene, polyvinylchloride, polycarbonate, polytetrafluoroethylene (PFTE), polyethylene terephthalate (PET), polystyrene (PS), and polymethylpentene. The projection 433 is preferably substantially sharp and rigid so as to readily break the seal 448 for releasing adhesive 450 from the container 440. Suitable materials for the projection 423 include but not limited to high density polyethylene (HDPE), polypropylene, polyvinylchloride, polycarbonate, polytetrafluoroethylene (PFTE), polyethylene terephthalate (PET), polystyrene (PS), and polymethylpentene.

The seal 448, which may be a frangible foil, is preferably heat-sealed to the container 440. The seal 448 may be fabricated from any suitable materials, which may include, but are not limited to, aluminum foil, plastic membrane, laminated aluminum foil, plastic wrap, waxed paper, oiled paper, or other materials that may form a seal without inducing premature polymerization of the adhesive 450. Laminated aluminum foil may be composed of at least two layers of different materials which include, but are not limited to, aluminum, acrylonitrile copolymer, low density polyethylene, low density polypropylene, polyethylene teraphthalate, and the like. In some preferred aspects, a laminated aluminum foil with acrylonitrile copolymer as the inner layer is used to construct the seal 448.

The applicators 180, 280, 380, and 480 described in this specification may be used to apply adhesive materials. Preferred adhesive materials include those that are readily polymerizable, e.g., anionically polymerizable and/or free radical polymerizable. The adhesive 150, 250, 350, or 450 is preferably a 1,1-disubstituted ethylene monomer, e.g., a cyanoacrylate monomer. In some preferred aspects, the adhesive include one or more polymerizable cyanoacrylate monomers, and/or reactive oligomers of cyanoacrylate. Such cyanoacrylate monomers are readily polymerizable, e.g., anionically polymerizable and/or free radical polymerizable, to form polymers. Cyanoacrylate monomers suitable for use include, but are not limited to, 1,1-disubstituted ethylene monomers of formula I:

$$HRC = CXY \quad (I)$$

wherein X and Y are each strong electron withdrawing groups, and R is H, —CH═CH$_2$, or a $C_1$-$C_4$ alkyl group. Examples of monomers within the scope of formula (I) include alpha-cyanoacrylates, vinylidene cyanides, $C_1$-$C_4$ alkyl homologues of vinylidene cyanides, dialkyl methylene malonates, acylacrylonitriles, vinyl sulfinates and vinyl sulfonates of the formula CH$_2$═CX'Y wherein X' is —SO$_2$R' or —SO$_3$R' and Y' is —CN, —COOR', —COCH$_3$, —SO$_2$R' or —SO$_3$R', and R' is H or hydrocarbyl. Preferred monomers of formula (I) are alpha-cyanoacrylates. These monomers are known in the art and have the formula II:

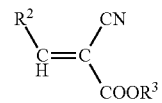

wherein R2 is hydrogen and R3 is a hydrocarbyl or substituted hydrocarbyl group; a group having the formula —R$^4$—O—R$^5$—O—R$^6$, wherein R$^4$ is a 1,2-alkylene group having 2-4 carbon atoms, R$^5$ is an alkylene group having 2-12 carbon atoms, and R$^6$ is an alkyl group having 1-6 carbon atoms; or a group having the formula:

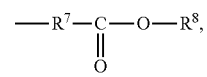

wherein R$^7$ is:

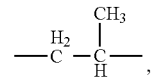

or —[C(CH$_3$)$_2$]$_n$—
wherein n is 1-14, preferably 1-8 carbon atoms and R$^8$ is an organic moiety.

Examples of suitable hydrocarbyl and substituted hydrocarbyl groups include straight chain or branched chain alkyl groups having 1-16 carbon atoms; straight chain or branched chain C1-C16 alkyl groups substituted with an acyloxy group, a haloalkyl group, an alkoxy group, a halogen atom, a cyano group, or a haloalkyl group; straight chain or branched chain alkenyl groups having 2 to 16 carbon atoms; straight chain or branched chain alkynyl groups having 2 to 12 carbon atoms cycloalkyl groups; arylalkyl groups; alkylaryl groups; and aryl groups.

The organic moiety R$^8$ may be substituted or unsubstituted and may be a straight chain, branched or cyclic, saturated, unsaturated or aromatic. Examples of such organic moieties include C1-C8 alkyl moieties, C2-C8 alkenyl moieties, C2-C8 alkynyl moieties, C3-C12 cycloaliphatic moieties, aryl moieties such as phenyl and substituted phenyl, and arylalkyl moieties such as benzyl, methylbenzyl and phenylethyl. Other organic moieties include substituted hydrocarbon moieties, such as halo (e.g., chloro-, fluoro- and bromo-substituted hydrocarbons) and oxy- (e.g., alkoxy substituted hydrocarbons) substituted hydrocarbon moieties. Preferred organic radicals are alkyl, alkenyl and alkynyl moieties having from 1 to about 8 carbon atoms, and halo-substituted derivatives thereof. Particularly preferred are alkyl moieties of 4 to 8 carbon atoms. In the cyanoacrylate monomer of formula (II), R$^8$ is preferably an alkyl group having 1-10 carbon atoms or a group having the formula -AO R$^9$, wherein A is a divalent straight or branched chain alkylene or oxyalkylene moiety having 2-8 carbon atoms, and R$^9$ is a straight or branched alkyl moiety having 1-8 carbon atoms. The preferred alpha-cyanoacrylate monomers used in this invention are 2-octyl cyanoacrylate, dodecyl cyanoacrylate, 2-ethylhexyl cyanoacrylate, butyl cyanoacrylate, methyl cyanoacrylate, 3-methoxybutyl cyanoacrylate, 2-butoxyethyl cyanoacrylate, 2-isopropoxyethyl cyanoacrylate, or 1-methoxy-2-propyl cyanoacrylate, or a combination thereof.

The applicators 180, 280, 380, and 480 and variations thereof, may be used, for example, to apply adhesive materials to different substrates. Suitable substrates include, but are not limited to, living tissues (e.g., skin), plastics, metals, wood, ceramics, fabrics, paper, or any surface in need of adherence to another surface. In preferred aspects, the adhesive materials that are packaged in the applicators may be used as tissue adhesives for wound closure or as microbial sealant to prevent surgical site infection. For example, the adhesives as applied via an applicator 180, 280, 380, or 480 can be used for closing surgical incisions, dressing traumatically lacerated tissues, dressing burns, covering superficial or skin surface wounds, and applying onto surgical incision site before surgery to provide in situ and post-surgery inhabitation of surgical site infections.

The adhesive materials may be bioabsorbable, and thus may be completely degraded, eroded, and/or gradually absorbed or eliminated by the body when exposed to a body fluid such as blood. Bioabsorbable adhesives can be used in many different applications including but not limited to general wound closure, endoscopic surgery, cardiac surgery, hernia surgery, artheroscopic surgery. Bioabsorbable adhesives preferably comprise one or more cyanoacrylates, or a composition thereof. A bioabsorbable adhesive composition may comprise alkoxyalkyl cyanoacrylate and polyethylene glycol. Said bioabsorbable adhesive compositions may also comprise a mixture of alkyl cyanoacrylate, alkoxyalkyl cyanoacrylate and polyethylene glycol. A preferred alkoxyalkyl cyanoacrylate is methoxyisopropyl cyanoacrylate. Other bioabsorbable adhesives may include copolymers of alkyl cyanoacrylate or alkoxyalkyl cyanoacrylate with other biocompatible monomers such as trimethylene carbonate, alkylene glycol, glycolide, lactide, $\epsilon$-caprolactone, and dioxane.

The cyanoacrylate monomers and compositions thereof can be prepared according to methods known in the art; see, e.g., U.S. Pat. Nos. 2,721,858 and 3,254,111. One such process includes, for example, reacting a cyanoacetate with formaldehyde in the presence of a basic condensation catalyst at an elevated temperature to produce a low molecular weight polymer. A de-polymerization (or cracking) step is followed under high temperature and high vacuum in the presence of acidic and anionic inhibitors, yielding a crude monomer that can be distilled under high temperature and high vacuum in the presence of radical and acidic inhibitors.

The materials used to construct the components and portions of the applicators 180, 280, 380, and 480 are preferably radiation-stable under the maximum dosage of E-beam, Gamma, and X-ray sterilization. The exceptional barrier properties offered by acrylonitrile copolymer make it an ideal inner layer material for use in construction of package bodies to sterilize adhesive compositions using radiation sterilization techniques. The inner layer of acrylonitrile copolymer provides high barrier properties which ensure the stability of the liquid adhesive compositions stored therein. Acrylonitrile copolymer offers a high barrier to oxygen at all levels of relative humidity. This ensures that a consistently high barrier to oxygen is maintained, regardless of the humidity of the surrounding environment. In addition, the water vapor barrier properties of acrylonitrile copolymer are comparable to other plastic packaging materials and are ultimately enhanced by the outer layer secured thereto. All of the properties of acrylonitrile copolymer enable it to be a suitable material as the package body for sterilizing cyanoacrylates via radiation sterilization technique.

The dose of radiation applied should be sufficient enough to sterilize both the applicator 180, 280, 380, or 480 and the adhesive 150, 250, 350, or 450 stored inside. In some embodiments, the E-beam radiation can be in a suitable dosage of from about 5 to about 50 kGy, preferably from about 10 to about 30 kGy, and more preferably from about 12 to about 25 kGy. The dose of X-ray applied to the adhesive stored in said applicators is in the range of about 5 kGy to about 40 kGy, preferably in the range of about 5 kGy to about 30 kGy, more preferably about 5 kGy to about 25 kGy. Gamma radiation for the adhesives packaged in the preferred applicators can be in a suitable dosage of from about 5 to about 50 kGy, preferably about 5 to about 40 kGy, and more preferably from about 5 to about 25 kGy.

The adhesive 150, 250, 350, or 450 stored in the applicators 180, 280, 380, or 480 remains substantially uncured and unpolymerized upon E-beam, Gamma, or X-ray sterilization. After radiation sterilization, the adhesive 150, 250, 350, or 450 may have a shelf-life (e.g., maintained without initiation of polymerization) of at least about 6 months, more preferably at least about 12 months, and more preferably at least about 24 months. The shelf-life stability of liquid adhesive compositions in various said applicators sterilized by different radiation sterilization techniques may be measured and established, for example, by an accelerated aging study at 80° C. over a period of days. For example, an aging study may be carried out at 80° C. for a period of 13 days. Based on the American Society for Testing and Materials' ASTM F1980 standards, 13 days accelerated aging at 80° C. correlates to 2 years of shelf life at ambient temperatures, and 1 day of accelerated aging at 80° C. is equal to 56 days at ambient temperature.

In order to reduce the bioburden, the cyanoacrylate adhesive compositions stored in the applicators 180, 280, 380, or 480 may be filtered through a 0.2 µm filter prior to different radiation sterilizations. The applicators that utilize secondary packaging (e.g., the overpack) may also be sterilized with heat and/or ethylene oxide prior to the final radiation.

A sterility assurance level (SAL) should be obtained at a minimum of $10^{-3}$, which means that the probability of a single unit being non-sterile after sterilization is 1 in 1000. In some preferred embodiments, the sterility assurance level may be at least $10^{-6}$. The sterility of the cyanoacrylate adhesives packaged in various applicators after radiation sterilization may be analyzed by Bacteriostasis and Fungistasis tests. For example, after testing with challenging microorganisms such as *Bacillus subtilis, Candida albicans*, and *Aspergillus niger*, no growth of the microorganisms for the cyanoacrylate adhesive in the applicators after radiation sterilization indicates the sterility of the cyanoacrylate adhesive.

The cyanoacrylate monomers may be stabilized by using a combination of free radical and anionic stabilizers before storing into the various applicators 180, 280, 380. Suitable free radical stabilizers include without limitation; butylated hydroxy anisole (BHA); hydroquinone; catechol; hydroquinone monomethyl ether and hindered phenols such as butylated hydroxyanisol; 4-ethoxyphenol; butylated hydroxytoluene (BHT, 2,6-di-tert-butyl butylphenol), 4-methoxyphenol (MP); 3methoxyphenol; 2-tert-butyl-4methoxyphenol; and 2,2-methylene-bis-(4-methyl-6-tert-butylphenol). The stabilizers may be present in an amount of 200 ppm to 15000 ppm, preferably 1000 ppm to 10000 ppm, and more preferably 2000 ppm to 8000 ppm.

Suitable anionic stabilizers for adhesives stored in the applicators 180, 280, 380, or 480 may include, but are not limited to, perchloric acid, hydrochloric acid, hydrobromic acid, sulfur dioxide, toluenesulfonic acid, fluorosulfonic acid, phosphoric acid, ortho, meta, or para-phosphoric acid, trichloroacetic acid, and sulfuric acid. The anionic stabilizer may be present in an amount of about 2 ppm to about 500 ppm, preferably about 10 ppm to about 200 ppm.

In some embodiments, the cyanoacrylate adhesive may further contain small amounts of colorants such as dyes or pigments. Suitable dyes include derivatives of anthracene and other complex structures, specifically, without limitation, 1-hydroxy-4-[4-methylphenylamino]-9,10 anthracenedione (D&C violet No. 2); 9-(ocarboxyphenyl)-6-hydroxy-2,4,5,7-tetraiodo-3H-xanthen-3-one-, disodium salt, monohydrate (FD&C Red No. 3); disodium salt of 6-hydroxy-5-[(4-sulfophenyl)axo]-2-naphthalene-sulfonic acid (FD&C Yellow No. 6,); 2-(1,3dihydro-3-oxo-5-sulfo-2H-indole-2-ylidine)-2,3-dihydro-3oxo-1H-ind-ole-5 sulfonic acid disodium salt (FD&C Blue No. 2); and 1,4-bis(4methylanilino)anthracene-9,10-dione (D&C Green No. 6). The preferred dyes are D&C Violet No. 2, FD&C Blue No. 2, and D&C Green No. 6.

A polymerization accelerator may be included in the cyanoacrylate adhesive materials. Suitable polymerization accelerators may include, but are not limited to, calixarenes and oxacalixarenes, silacrowns, crownethers, cyclodextrin and its derivatives, polyethers, aliphatic alcohol, various aliphatic carboxylic acid esters, benzoyl peroxide, amine compounds such as are triethyl amine, diethyl amine, butyl amine, isopropyl amine, tributyl amine, N,N,-dimethyl aniline, N,N-diethyl aniline, N,N-dimethyl-p-toluidine, N,N-dimethyl-m-toluidine, N,N-dimethyl-o-toluidine, dimethyl benzyl amine, pyridine, picoline, vinyl pyridine, ethanolamine, propanolamine and ethylene diamine, quaternary ammonium salts such as alkyl ammonium salts, amide-bonded ammonium salts, ester-bonded ammonium salts, ether-bonded ammonium salts and alkylimidazolinium salts, cyclosulfur compounds and derivatives, and polyalkylene oxides and derivatives.

In some embodiments, the cyanoacrylate adhesive compositions may optionally comprise an antimicrobial agent in an effective amount. The antimicrobial agent may be released from the polymer film of the adhesives formed on human or animal skins to inhibit microbial growth and prevent wound or surgical site infections. Suitable antimicrobial agents include, but are not limited to, antibacterial agents such as chlorhexidine and its salts, typical antibiotics, copolymers of vinylpyrrolidone and vinyl acetate, antiseptics, the iodine containing polymer such as povidone iodine, biguanidine compounds, phenol compounds such as 5-chloro-2-(2,4-dichlorophenoxy)phenol, acridine compounds, quaternary ammonium compounds such as benzalkonium chloride, cetylpridospores and zephiran, copolymers of vinylpyrrolidone and vinyl acetate cross-linked with polyisocyanates, heavy metal salts such as silver nitrate, and aldehyde compounds such as glutaraldhyde.

The cyanoacrylate may optionally contain thickening agents. Suitable thickening agents include, but are not limited to, polycaprolactone, copolymers of alkylacrylate and vinyl acetate, polyalkyl methacrylates, polyalkyl acrylates, lactic-glycolic acid copolymers, lactic acid-caprolactone copolymers, polyorthoesters, copolymers of alkyl methacrylates and butadiene, polyoxalates, and triblock copolymers of polyoxypropylene flanked by two hydrophilic chains of polyoxyethylene. Preferred thickening agents include a partial polymer of cyanoacrylate as disclosed in U.S. patent application Ser. No. 12/214,791, and triblock copolymers of polyoxyalkylene as disclosed in U.S. patent application Ser. No. 12/214,794. Preferably the thickening agent is miscible in cyanoacrylate monomer compositions at room temperature.

The cyanoacrylate adhesive may optionally include at least one plasticizing agent that imparts flexibility to the polymer formed from the monomer. The plasticizing agent preferably does not contain any moisture and should not adversely affect the stability of said cyanoacrylate compositions. Examples of suitable plasticizers include, but are not limited to, tributyl citrate (TBC), acetyl tributyl citrate (ATBC), dimethyl sebacate, diethylsebacate, triethyl phosphate, tri(2-ethyl-hexyl) phosphate, tri(p-cresyl)phosphate, diisodecyl adipate (DIDA), glyceryl triacetate, glyceryl tributyrate, dioctyl adipate (DICA), isopropyl myrisate, butyl sterate, lauric acid, trioctyl trimelliate, dioctyl glutatrate (DICG) and mixtures thereof. Tributyl citrate, diisodecyl adipate and acetyl tributyl citrate are preferred plasticizers, which when present are in an amount of up to thirty percent (30%) by weight of the liquid adhesive composition. The amount to be used can be determined by one of ordinary skills in the art, using known techniques without undue experimentation.

The cyanoacrylate adhesive may also optionally include preservatives. A preservative may be paraben such as alkyl parabens and salts thereof, ethylparaben, methylparaben, methylparaben sodium, propylparaben sodium, propylparaben, butylparaben, and the like. Other suitable preservatives include hydroquinone, pyrocatechol, resorcinol, 4-n-hexyl resorcinol, benzoic acid, benzyl alcohol, chlorobutanol, dehydroacetic acid, o-phenylphenol, phenol, phenylethyl alcohol, potassium benzoate, potassium sorbate, sodium benzoate, sodium dehydroacetate, sodium propionate, sorbic acid, thimerosal, thymol, cresols, phenylmercuric compounds such as phenylmercuric borate, and phenylmercuric nitrate.

The invention is not limited to the embodiments described and exemplified above, but is capable of variation and modification within the scope of the appended claims.

What is claimed is:

1. An applicator for storing and dispensing an adhesive comprising:
    a) a container comprising walls defining a chamber comprising a proximal end and a distal end and an opening at the distal end of the chamber, said walls comprising a single layer of a copolymer of acrylonitrile and methyl acrylate or comprising multiple layers with the innermost layer comprising a copolymer of acrylonitrile and methyl acrylate, said chamber further comprising a frangible distal seal, a frangible middle seal, and frangible a proximal seal covering the distal end of the chamber, said proximal seal having a side in communication with an adhesive stored in the chamber between the proximal seal and the proximal end of the chamber, said adhesive comprising a cyanoacrylate monomer, a free radical stabilizer in an amount of 200 ppm to 15,000 ppm, and an anionic stabilizer in an amount of about 10 ppm to about 200 ppm;
    b) a body comprising a proximal end and a distal end, a flange comprising at least one hole, a channel in communication with the hole, said channel extending through the body, and having an opening at the distal end of the body, and a grip capable of constricting the channel when inward pressure is applied to the grip,
    wherein the proximal end of the body is positioned between the middle frangible seal and the proximal frangible seal of the chamber when the applicator is not activated, and is capable of penetrating the proximal frangible seal when the body and the container are compressed together; and
    c) a porous tip in communication with the opening at the distal end of the channel;
    wherein the applicator is activated by compressing the body and the container together whereupon the flange penetrates the proximal seal and allows the adhesive to flow into the hole, through the channel, and out of the porous tip, and wherein at least the container is sterilized by radiation, and the adhesive stored in the container does not cure upon radiation exposure and for at least about twelve months of shelf storage thereafter.

2. The applicator of claim 1, wherein the cyanoacrylate monomer comprises a monomer of 2-octyl cyanoacrylate, dodecyl cyanoacrylate, 2-ethylhexyl cyanoacrylate, butyl cyanoacrylate, methyl cyanoacrylate, 3-methoxybutyl cyanoacrylate, 2-butoxyethyl cyanoacrylate, 2-isopropoxyethyl cyanoacrylate, 1-methoxy-2-propyl cyanoacrylate, or a combination thereof.

3. The applicator of claim 1, wherein the radiation is gamma radiation, electron beam radiation, or x-ray radiation.

4. The applicator of claim 1, wherein the adhesive stored in the chamber of the container does not cure upon radiation exposure and for at least about twenty four months of shelf storage thereafter.

5. The applicator of claim 1, wherein the porous tip comprises a swab, sponge, foam, or a brush.

6. The applicator of claim 1, further comprising a tip overlay removably placed over top of the porous tip.

7. An applicator for storing and dispensing an adhesive comprising:
   a) a flexible handle comprising a distal end, a housing for containing a removable adhesive container, and a female end of a luer lock at the distal end of the handle;
   b) a body comprising a proximal end and a distal end, a male end of a luer lock at the proximal end of the body, said male end being capable of connecting to the female end at the distal end of the handle, and a channel extending through the body, and having an opening at the distal end of the body;
   c) a porous tip in communication with the channel opening at the distal end of the body; and
   d) a removable container comprising a distal end, and comprising a single layer of a copolymer of acrylonitrile and methyl acrylate or comprising multiple layers with the inner-most layer comprising a copolymer of acrylonitrile and methyl acrylate, said container being capable of fitting within the housing, and further comprising a frangible seal covering the distal end of the container and having a side in communication with an adhesive stored in the container, said adhesive comprising a cyanoacrylate monomer, a free radical stabilizer in an amount of 200 ppm to 15,000 ppm, and an anionic stabilizer in an amount of about 10 ppm to about 200 ppm;
   wherein the applicator is activated by compromising the frangible seal whereupon the adhesive may flow into and through the channel and out of the porous tip, and wherein at least the container is sterilized by radiation, and the adhesive stored in the container does not cure upon radiation exposure and for at least about twelve months of shelf storage thereafter.

8. The applicator of claim 7, wherein the cyanoacrylate monomer comprises a monomer of 2-octyl cyanoacrylate, dodecyl cyanoacrylate, 2-ethylhexyl cyanoacrylate, butyl cyanoacrylate, methyl cyanoacrylate, 3-methoxybutyl cyanoacrylate, 2-butoxyethyl cyanoacrylate, 2-isopropoxyethyl cyanoacrylate, 1-methoxy-2-propyl cyanoacrylate, or a combination thereof.

9. The applicator of claim 7, wherein the container is a stick pack container.

10. The applicator of claim 7, wherein the frangible seal comprises aluminum foil laminated with a copolymer of acrylonitrile and methyl acrylate on the side in communication with the adhesive stored in the container.

11. The applicator of claim 7, wherein the radiation is gamma radiation, electron beam radiation, or x-ray radiation.

12. The applicator of claim 7, wherein the adhesive stored in the chamber of the container does not cure upon radiation exposure and for at least about twenty four months of shelf storage thereafter.

13. The applicator of claim 7, wherein the porous tip comprises a swab, sponge, foam, or a brush.

14. The applicator of claim 7, further comprising a tip overlay removably placed over top of the porous tip.

15. An applicator for storing and dispensing an adhesive comprising:
   a) a container comprising walls defining a chamber having a distal end and an opening at the distal end of the chamber, said walls comprising a single layer of a copolymer of acrylonitrile and methyl acrylate or comprising multiple layers with the inner-most layer comprising a copolymer of acrylonitrile and methyl acrylate, a frangible seal covering the opening and having a side in communication with the chamber, an adhesive comprising a cyanoacrylate monomer, a free radical stabilizer in an amount of 200 ppm to 15,000 ppm, and an anionic stabilizer in an amount of about 10 ppm to about 200 ppm stored in the chamber, and optionally, screw threads on the exterior of the walls of the container;
   b) a body comprising a proximal end and a distal end, a cavity at the proximal end of the body, a channel having a proximal end and a distal and, said channel being in communication with the cavity, extending through the body, and having an opening at the distal end of the channel, a grip capable of constricting the channel when inward pressure is applied to the grip, at least one projection in the cavity, wherein the projection is capable of penetrating the frangible seal when the body and the container are compressed together, and optionally, screw threads on the walls of the cavity capable of engaging the screw threads on the exterior of the walls of the container; and
   c) a porous tip in communication with the opening at the distal end of the channel;
   wherein the applicator is activated by compressing the body and the container together whereupon the projection penetrates the frangible seal and allows the adhesive to flow into and through the channel and out of the porous tip, and wherein at least the container is sterilized by radiation, and the adhesive stored in the chamber of the container does not cure upon radiation exposure and for at least about twelve months of shelf storage thereafter.

16. The applicator of claim 15, wherein the cyanoacrylate monomer comprises a monomer of 2-octyl cyanoacrylate, dodecyl cyanoacrylate, 2-ethylhexyl cyanoacrylate, butyl cyanoacrylate, methyl cyanoacrylate, 3-methoxybutyl cyanoacrylate, 2-butoxyethyl cyanoacrylate, 2-isopropoxyethyl cyanoacrylate, 1-methoxy-2-propyl cyanoacrylate, or a combination thereof.

17. The applicator of claim 15, wherein the frangible seal comprises aluminum foil laminated with a copolymer of acrylonitrile and methyl acrylate on the side in communication with the chamber.

18. The applicator of claim 15, wherein the radiation is gamma radiation, electron beam radiation, or x-ray radiation.

19. The applicator of claim 15, wherein the adhesive stored in the chamber of the container does not cure upon radiation exposure and for at least about twenty four months of shelf storage thereafter.

20. The applicator of claim 15, wherein the porous tip comprises a swab, sponge, foam, or a brush.

21. The applicator of claim 15, wherein the container comprises screw threads on the exterior of the walls of the container and the cavity comprises screw threads on the walls of the cavity, and the applicator is activated by screwing the body and the container together whereupon the projection penetrates the frangible seal and allows the adhesive to flow into and through the channel and out of the porous tip.

22. The applicator of claim 15, further comprising a tip overlay removably placed over top of the porous tip.

23. The applicator of claim 15, further comprising, a removable lock between the container and the body that prevents the body and the container from being compressed together and that, when removed, allows the body and the container to be compressed together.

24. The applicator of claim 1, further comprising, a removable lock between the container and the body that prevents the body and the container from being compressed together and that, when removed, allows the body and the container to be compressed together.

\* \* \* \* \*